(12) United States Patent
Imig et al.

(10) Patent No.: US 7,732,470 B2
(45) Date of Patent: *Jun. 8, 2010

(54) COMPOSITIONS AND METHODS FOR THE TREATMENT OF RENAL AND CARDIOVASCULAR DISEASE

(75) Inventors: John D. Imig, Wauwatosa, WI (US); John R. Falck, University Park, TX (US)

(73) Assignees: Medical College of Georgia Research Institute, Augusta, GA (US); Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/040,502

(22) Filed: Feb. 29, 2008

(65) Prior Publication Data

US 2008/0153889 A1 Jun. 26, 2008

Related U.S. Application Data

(63) Continuation-in-part of application No. 11/866,395, filed on Oct. 2, 2007.

(60) Provisional application No. 60/848,708, filed on Oct. 2, 2006.

(51) Int. Cl.
*A01N 43/78* (2006.01)

(52) U.S. Cl. .................. 514/369; 514/562; 514/564; 514/566; 514/557; 548/183; 554/51; 554/53; 554/63; 554/213; 554/223; 554/227; 562/557; 562/564; 562/565; 562/567; 562/587

(58) Field of Classification Search .................. 514/369, 514/562, 566, 564, 557; 548/183; 554/51, 554/53, 63, 213, 223, 227; 562/564, 565, 562/557, 567, 587
See application file for complete search history.

(56) References Cited

U.S. PATENT DOCUMENTS 6,890,925 B2 5/2005 Ingraham et al.
2006/0148744 A1 7/2006 Hammock et al.

OTHER PUBLICATIONS

Falck et al., "11, 12-Epoxyeicosatrienoic Acid (11, 12-EET): Structural Determinants for Inhibition of TNF-alpha-Induced VCAM-1 Expression," Bioorganic & Medicinal Chemistry Letter 13, 2003, 4011-4014.
Imig et al., "Enhanced renal microvascular reactivity to angiotensin II in hypertension is ameliorated by the sulfonimide analog of 11,12-epoxyeicosatrienoic acid," Journal of Hypertension, 2001, 19:983-992.
Imig, "Epoxide hydrolase and epoxygenase metabolites as therapeutic targets for renal diseases," Am J Physiol Renal Physiol, 2005, 289:F496-F503.
Zhao et al., "Decreased Renal Cytochrome P450 2C Enzymes and Impaired Vasodilation Are Associated With Angiotensin Salt-Sensitive Hypertension," Hypertension, 2003, 41:709-714.

*Primary Examiner*—Deborah D Carr
(74) *Attorney, Agent, or Firm*—Sutherland Asbill & Brennan LLP

(57) ABSTRACT

Derivative compounds of 11-nonyloxy-undec-8(Z)-eonic acid that mimic epoxide metabolites are provided. Also provided are compositions comprising a therapeutically effective amount of the derivative compounds. The present invention further provides methods for the use of such compositions for the treatment of renal or cardiovascular disease and/or related conditions.

15 Claims, 11 Drawing Sheets

COMPOSITIONS AND METHODS FOR THE TREATMENT OF RENAL AND CARDIOVASCULAR DISEASE

CROSS-REFERENCE TO RELATED APPLICATIONS

This application claims priority as a continuation-in-part to U.S. application Ser. No. 11/866,395 filed Oct. 2, 2007 and to U.S. Provisional Application Ser. No. 60/848,708 filed Oct. 2, 2006, the entire contents of which are hereby incorporated in their entirety.

ACKNOWLEDGMENT OF FEDERAL RESEARCH SUPPORT

This invention was made, at least in part, with Government support under NIH Grant Numbers HL-59699 to JI, GM31278 to JRF, and DK-38226 to JI and JRF, awarded by the National Institutes of Health, Accordingly, the United States Government has certain rights in this invention.

BACKGROUND OF THE INVENTION

1. Field of the Invention

This invention relates generally to compositions and methods for the treatment of renal and cardiovascular diseases. In particular, this invention relates to compositions comprising compounds that mimic epoxide metabolites and to methods for the use of such compositions for the treatment of renal or cardiovascular disease and/or related conditions, 2. Background Art A major cause of morbidity and mortality is the progression of organ damage associated with renal and cardiovascular diseases. The incidence of end-stage renal disease (ESRD) is escalating, and the two main diseases responsible for the increase in ESRD are diabetes and hypertension. In the case of diabetes, unused glucose remaining in the blood damages the nephrons, resulting in diabetic nephropathy. In patients with hypertension, small blood vessels in the kidney may become damaged and then cannot function properly to filter wastes. One contributing factor to end-organ damage is an impaired endothelium. Interestingly, endothelial dysfunction has been touted as a marker for unfavorable cardiovascular prognosis in humans.

Earlier studies have shown that endothelium-derived factors can act on vascular smooth muscle cells to relax or contract arteries. Nitric oxide and prostaglandins are the main products of the endothelial cells that relax the vascular smooth muscle. In addition, the endothelium releases one or more substances that relax vascular smooth muscle cells through membrane hyperpolarization (i.e., endothelium-derived hyperpolarizing factors (EDHFs)). A number of studies have provided evidence that this nitric oxide- and cyclooxygenase (COX)-independent endothelium-derived relaxing factor is a metabolite of the arachidonic acid cascade. It has been postulated that the unidentified EDHF hyperpolarized vascular smooth muscle cells by activating calcium-activated $K^+$ channels ($K_{Ca}$), but the identity of the EDHF(s) has been debated.

Cytochrome P-450 (CYP) metabolites produced by the endothelium have been shown to have antihypertensive properties. Epoxyeicosatrienoic acids (EETs) are produced by the kidney and act to increase renal blood flow and promote sodium secretion. It has been proposed that the EETs are endothelium-derived hyperpolarizing factors (EDHFs). Additionally, EETs have been demonstrated to have profibrinolytic effects, to have anti-inflammatory actions, and to inhibit smooth vascular muscle cell migration. The corresponding diols. vic-dihydroxyeicosatrienoic acids (DHETEs), lack significant renal vascular dilator activity. DHETEs are generated from EETs by the action of a soluble epoxide hydrolase (sEH), and in a number of vascular systems, the diols either have decreased actions or are devoid of activity.

Several EETs have been analyzed with respect to their ability to function as an EDHF. In particular, 5,6-EET is an EDHF candidate because it decreases renal perfusion pressure in the Wistar-Kyoto and spontaneously hypertensive (SHR) rats. In addition, 11,12-EET and 14,15-EET are the two epoxide metabolites of arachidonic acid that most consistently demonstrate vascular smooth muscle cell-relaxing properties and other cardiovascular protective activities. 11,12-EET acts on preglomerular vascular smooth muscle cells to dilate the arteriole. In addition, this epoxide metabolite activates renal microvascular smooth muscle cell $K_{Ca}$ channels and activates $K_{Ca}$ channels in cerebral and coronary vascular smooth muscle cells as well. ADP ribosylation is one intracellular mechanism that has been demonstrated to activate $K_{Ca}$ channels in coronary arteries. In addition, epoxides also have been shown to hyperpolarize platelets by activating $K_{Ca}$ channels. Renal microvascular activation of $K_{Ca}$ channels appears to be mediated by cAMP stimulation of protein kinase A because afferent arteriolar dilation to the sulfonamide analog of 11,12-EET was substantially reduced by protein kinase A inhibition. The $K_{Ca}$ channel- and protein kinase A-mediated dilator actions of 11,12-EET on afferent arterioles are consistent with the concept that 11,12-EET is an EDHF. Besides arterial endothelial cells, epoxyeicosatrienoic acid (EET) generation has been demonstrated in brain astrocytes, cardiac myocytes, airway tissues, the gastrointestinal tract, pancreas, and kidney. Vasodilation to EETs has been observed in renal, mesenteric, cerebral, pulmonary, and coronary arteries Abnormal regulation of kidney and vascular epoxide metabolites occurs in renal and cardiovascular diseases including, for example, type 1 and type 2 diabetes, hepatorenal syndrome, metabolic syndrome, insulin resistance syndrome, glomerullonephritis, hypertension, congestive heart failure, heart attack hypertensive heart disease, atherosclerosis, coronary artery disease, angina, ischemia, ischemic stroke, Raynaud's disease, and renal disease. The protective actions of the epoxide metabolites are diminished or lost in these disease states. Therefore, it would be advantageous to identify compounds that mimic the protective action of epoxide metabolites.

To date, various strategies have been employed for the treatment of renal and/or cardiovascular disease. For example, some researchers have focused on the role of soluble epoxide hydrolase (sEH) in renal and cardiovascular disease and inhibition of this enzyme as an avenue to increase EET levels. See, e.g., U.S. Pat. No. 6,890,925 Ingraham et al.; U.S. Publication No. 2006/0148744 to Hammock et al.; and Imig, 2005, Am. J. Physiol. Renal Physiol. 289:F496-F503. Although some methods have been achieved which effectively treat renal and cardiovascular disease, clearly more therapeutics are needed to treat a broader range of renal and/or cardiovascular diseases and conditions, as well as to increase the efficacy of the methods that already exist.

Therefore, what is needed in the art are new compounds and compositions for treating renal and/or cardiovascular diseases and conditions. What is also needed are methods for treating renal and/or cardiovascular diseases and conditions such as type 1 and type 2 diabetes, hepatorenal syndrome, metabolic syndrome, insulin resistance syndrome, glomerullonephritis, hypertension, congestive heart failure, heart attack, hypertensive heart disease, atherosclerosis, coronary artery disease, angina, ischemia, ischemic stroke, Raynaud's disease, and renal disease.

SUMMARY OF THE INVENTION

This invention fulfills in part the need to identify new, unique compounds, pharmaceutical compositions, and methods for treating renal and cardiovascular disease. In particular, the present invention describes compounds that are derivatives of 11-nonyloxy-undec-8(Z)-eonic acid that decrease blood pressure in an art-accepted animal model for hypertension. These and other embodiments of the invention will become apparent to one of skill in the art upon review of the description of the invention.

The invention provides compounds that are derivatives of 11-nonyloxy-undec-8(Z)-eonic acid or a pharmaceutically acceptable salt thereof, wherein the compound reduces blood pressure. In a preferred embodiment, the compound has the structural formula:

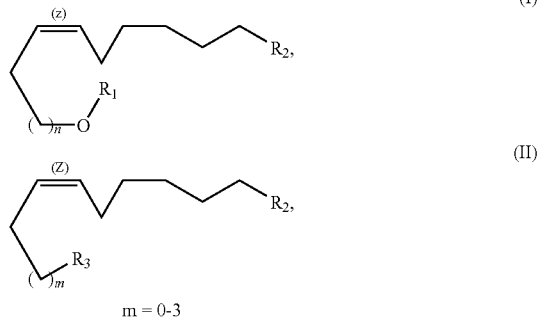

m = 0-3 or a pharmaceutically acceptable salt thereof, wherein
n is 1 to 4; m is 0 to 3
$R_1$ is selected from the group consisting of a linear or branched alkyl and cycloalkyl, each having up to 10 carbon atoms;
$R_2$, in each occurrence, is selected from the group consisting of linear or branched alkyl, cycloalkyl, alkyloxy, alkylthio, alkylamino, alkenyl, alkoxycarbonyl, carboxyalkylamide, thiazolidinyl-2,4-dione, or heterocyclyl, each optionally substituted with one or more halogen, OH, $CO_2H$, $NH_2$, alkoxy, alkylamine, $NO_2$, $SO_3$alkyl, alkylthio, alkylsulfinyl, or alkylsulfonyl, and each having up to 12 carbon atoms; and
$R_3$ is a $C_{6-9}$ epoxide;
wherein the compound reduced blood pressure. In certain embodiments, $R_2$ is selected from the group consisting of:

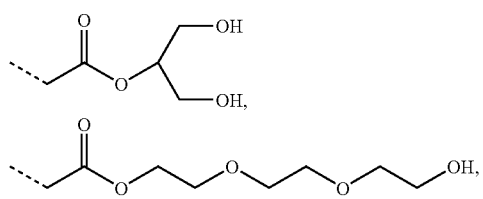

-continued

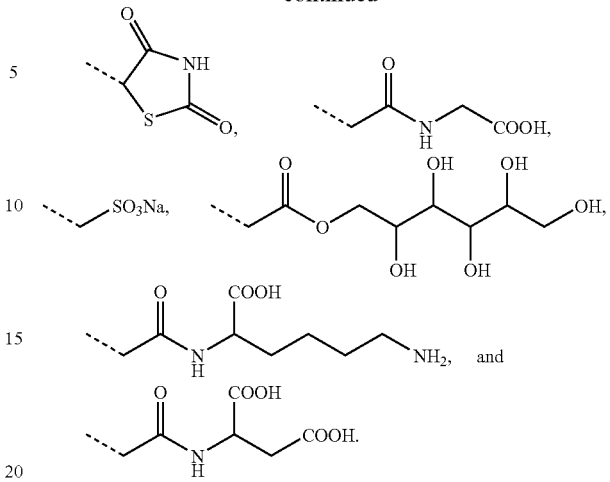

The invention also provides compositions comprising a therapeutically effective amount of a derivative of 11-nonyloxy-undec-8(Z)-eonic acid or a pharmaceutically acceptable salt or derivative thereof, wherein the compound reduces blood pressure. The invention further provides methods for using such compositions for the treatment of a renal and cardiovascular disease. In certain embodiments, the renal or cardiovascular disease is selected from type 1 and type 2 diabetes, hepatorenal syndrome, metabolic syndrome, insulin resistance syndrome, glomerulonephritis, hypertension, congestive heart failure, heart attack, hypertensive heart disease, atherosclerosis, coronary artery disease, angina, ischemia, ischemic stroke, and Raynaud's disease.

DETAILED DESCRIPTION OF THE INVENTION

Figure 1A:
FIG. 1A shows the effect of Ether-EET (11-nonyloxy-undec-8(Z)-enoic acid) on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1A:
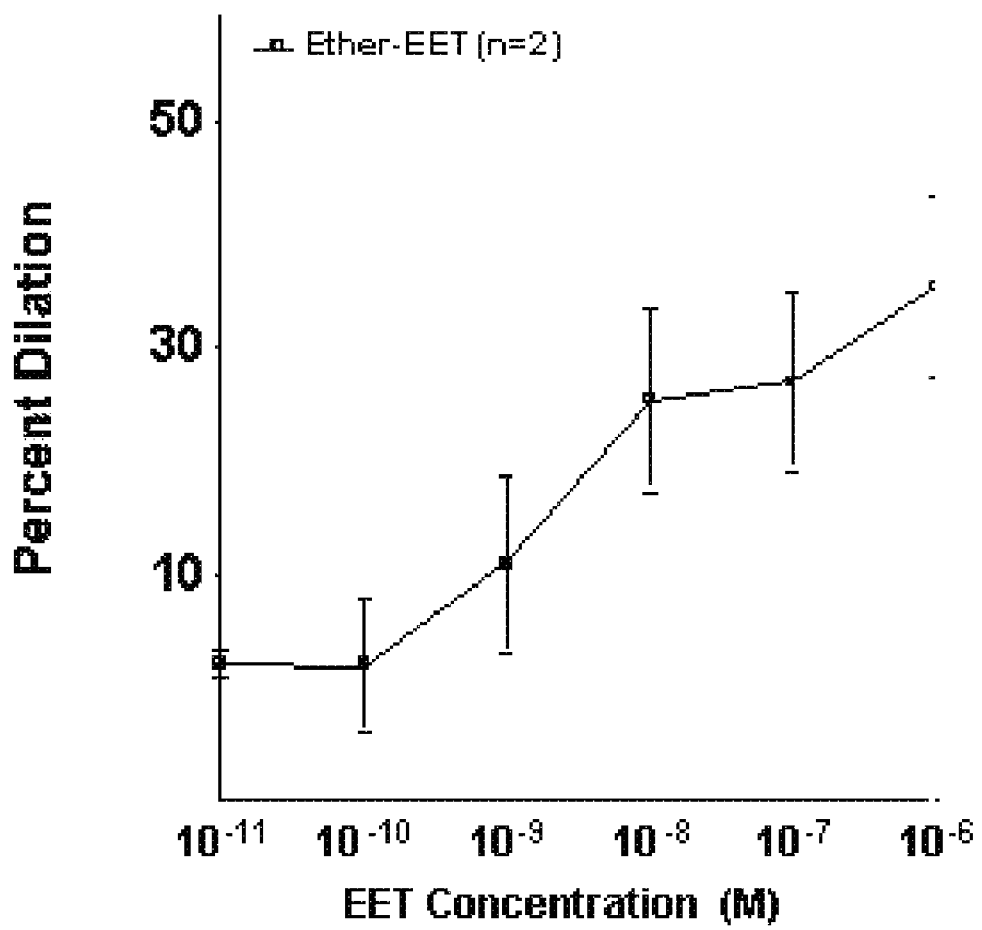
Figure 1B:
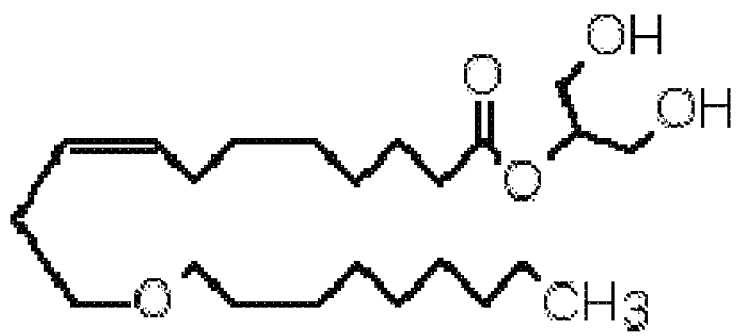
FIG. 1B shows the effect of the 11-nonyloxy-undec-8(Z)-enoic acid derivative TVR-I-302-21 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1B:
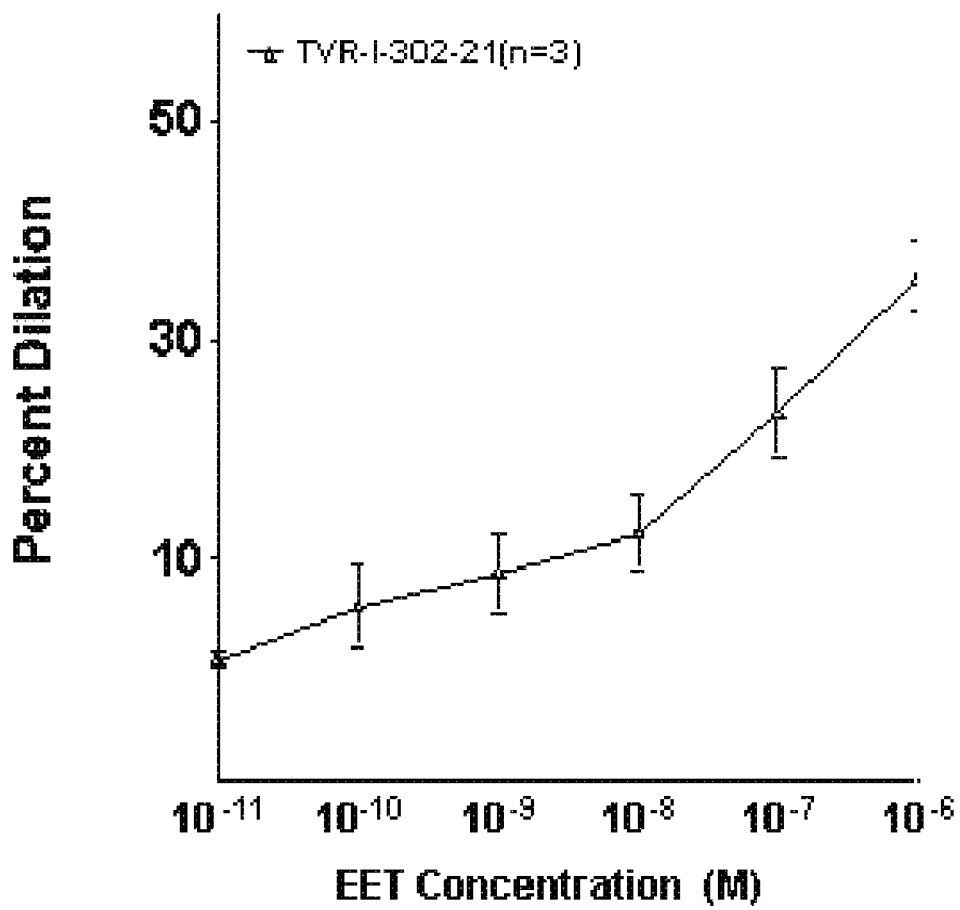
Figure 1C:
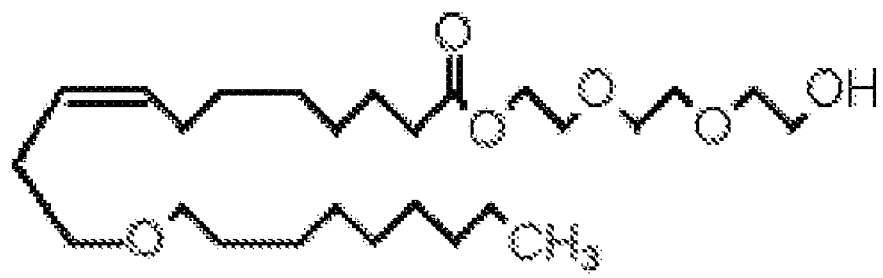
FIG. 1C shows the effect of the 11-nonyloxy-undec-8(Z)-enoic acid derivative TVR-I-276-21 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1C:
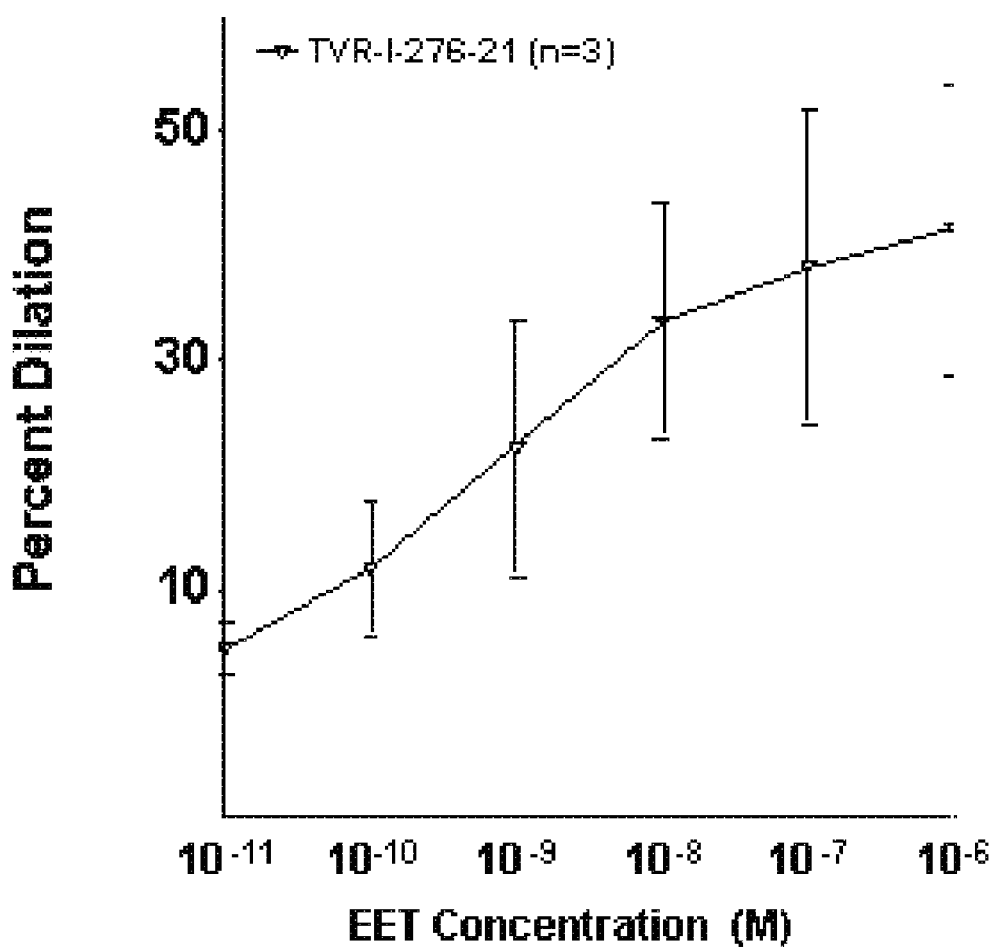
Figure 1D:
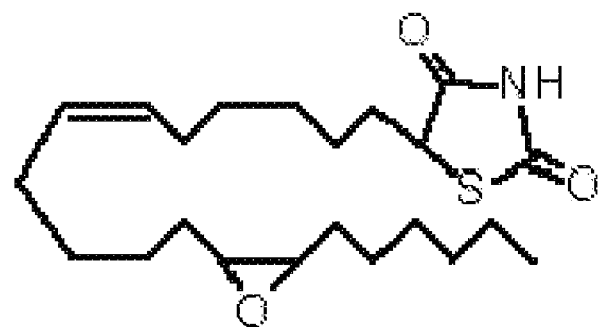
FIG. 1D shows the effect of the 11-nonyloxy-undec-8(Z)-enoic acid derivative TVR-I-221-30 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1D:
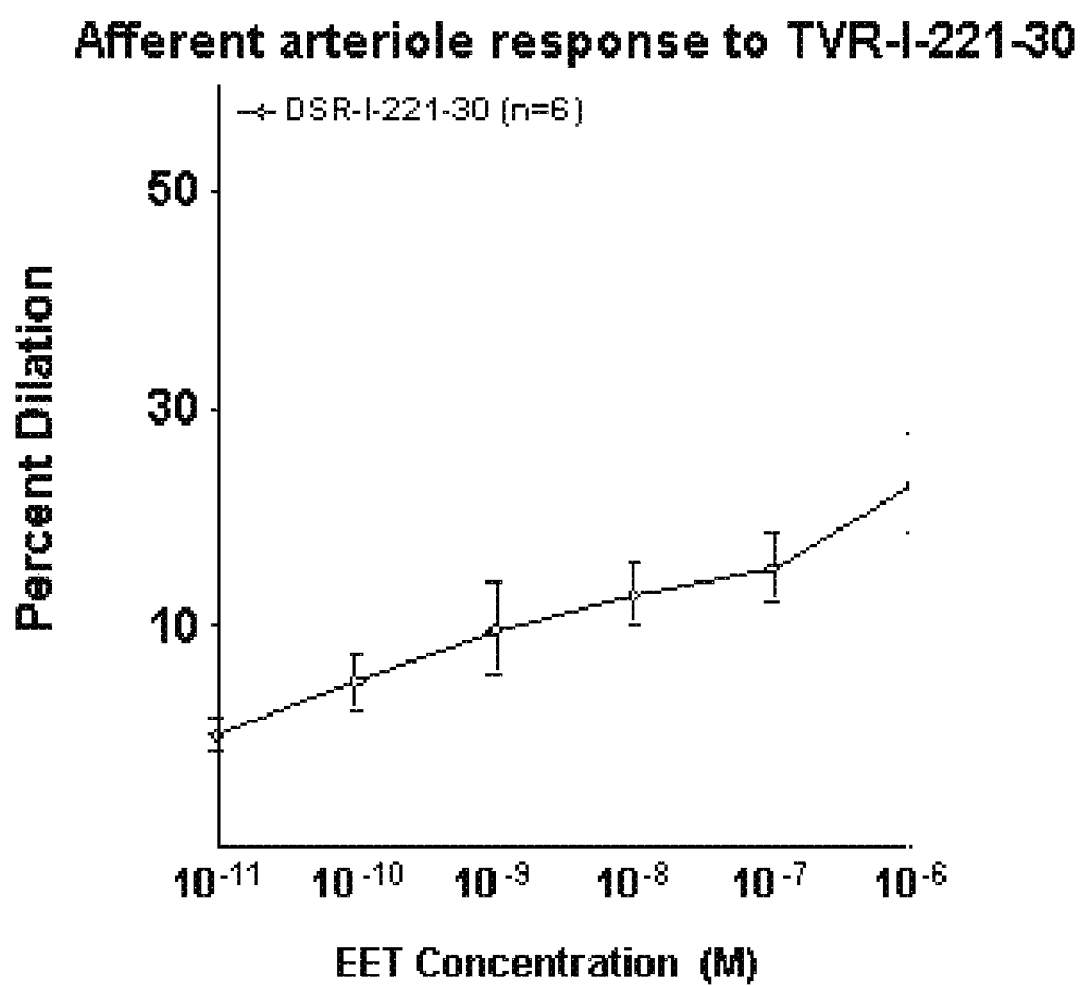
Figure 1E:
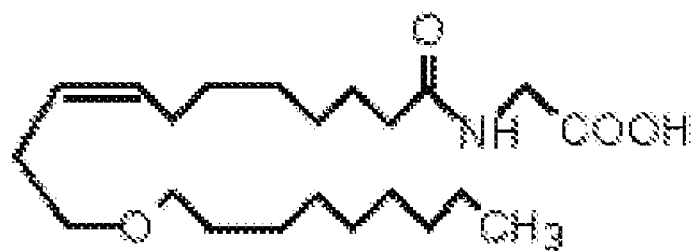
FIG. 1E shows the effect of the 11-nonyloxy-undec-8(Z)-enoic acid derivative TVR-I-285-21 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1E:
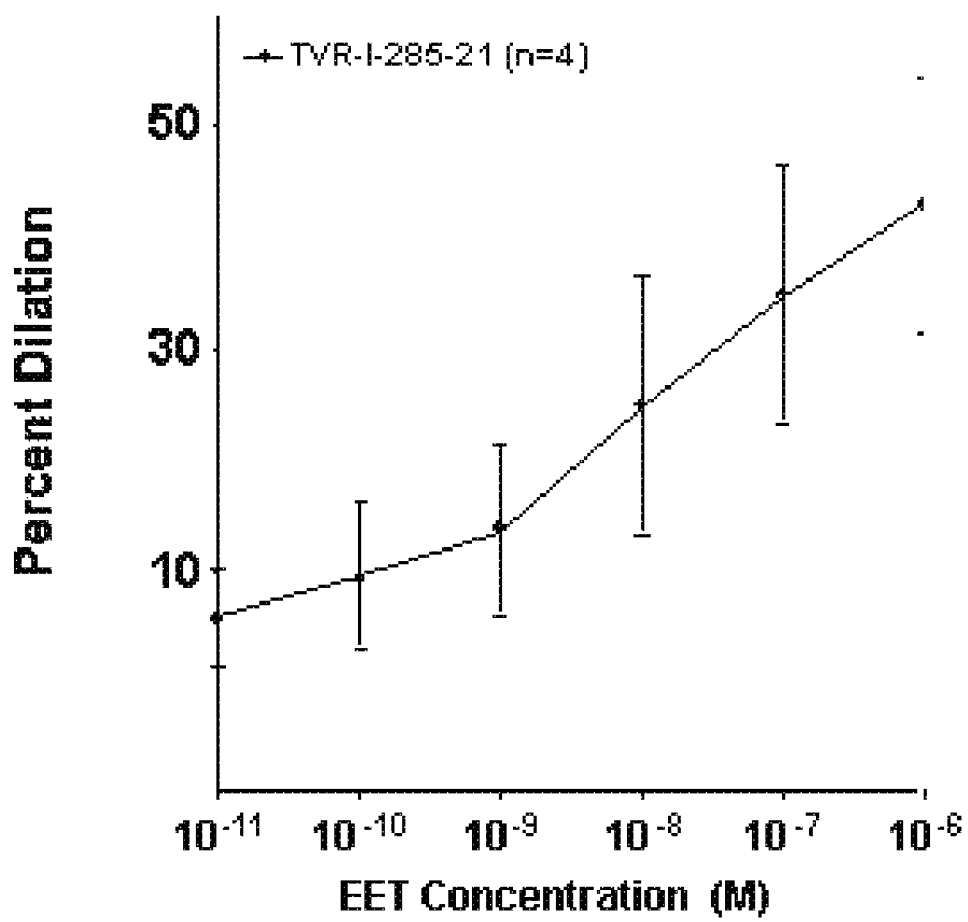
Figure 1F:
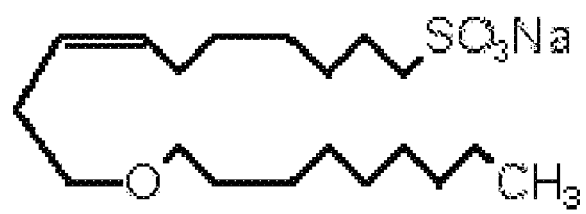
FIG. 1F shows the effect of the 11-nonyloxy-undec-8(Z)-enoic acid derivative TVR-II-007-20 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1F:
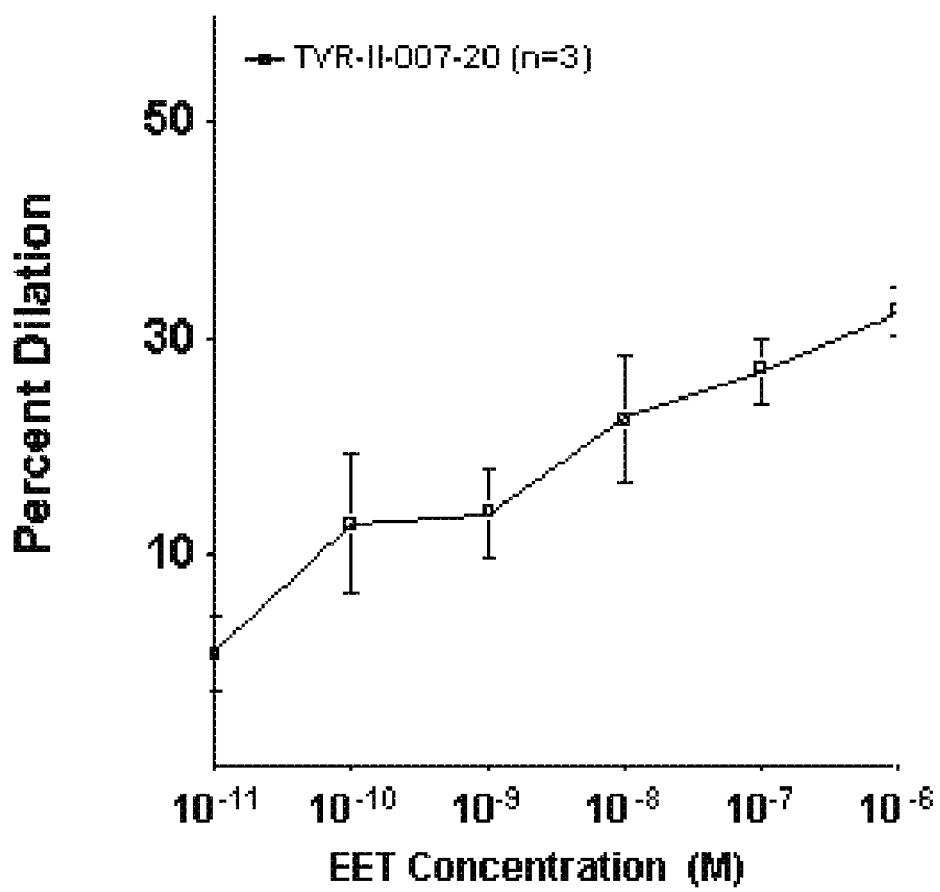
Figure 1G:
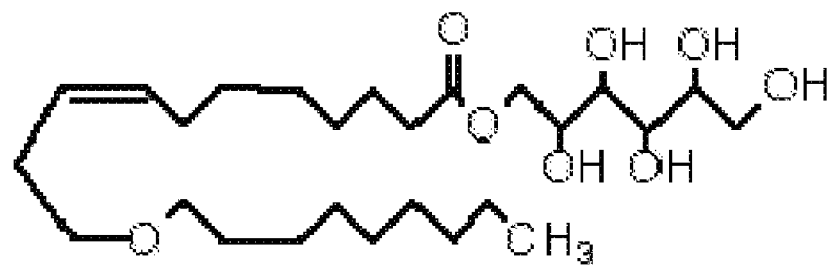
FIG. 1G shows the effect of the 11-nonyloxy-undec-8(Z)-enoic acid derivative TVR-I-280-21 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1G:
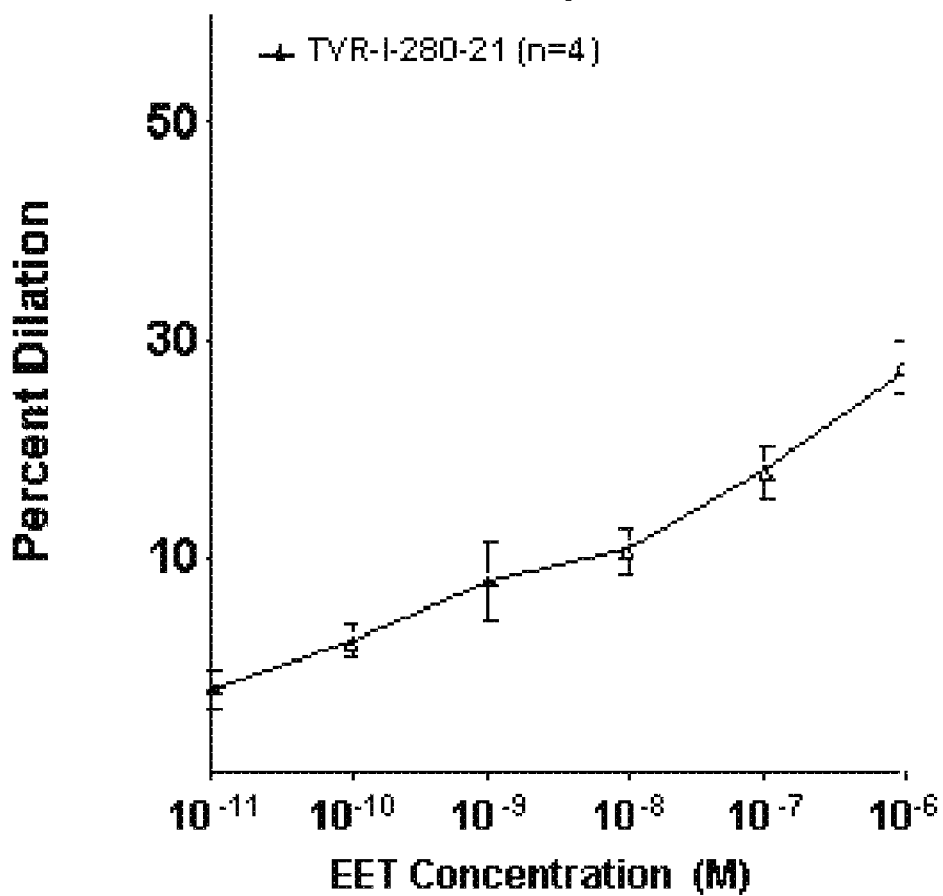
Figure 1H:
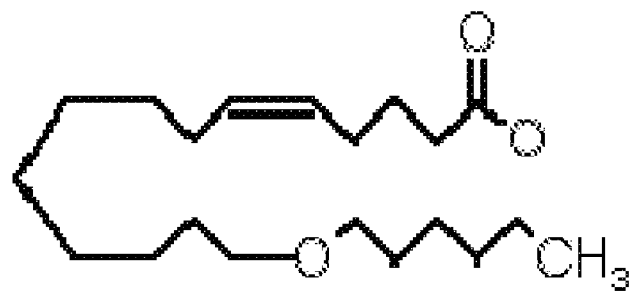
FIG. 1H shows the effect of the 11-nonyloxy-undec-8(Z)-enoic acid derivative SB-II-148-33 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1H:
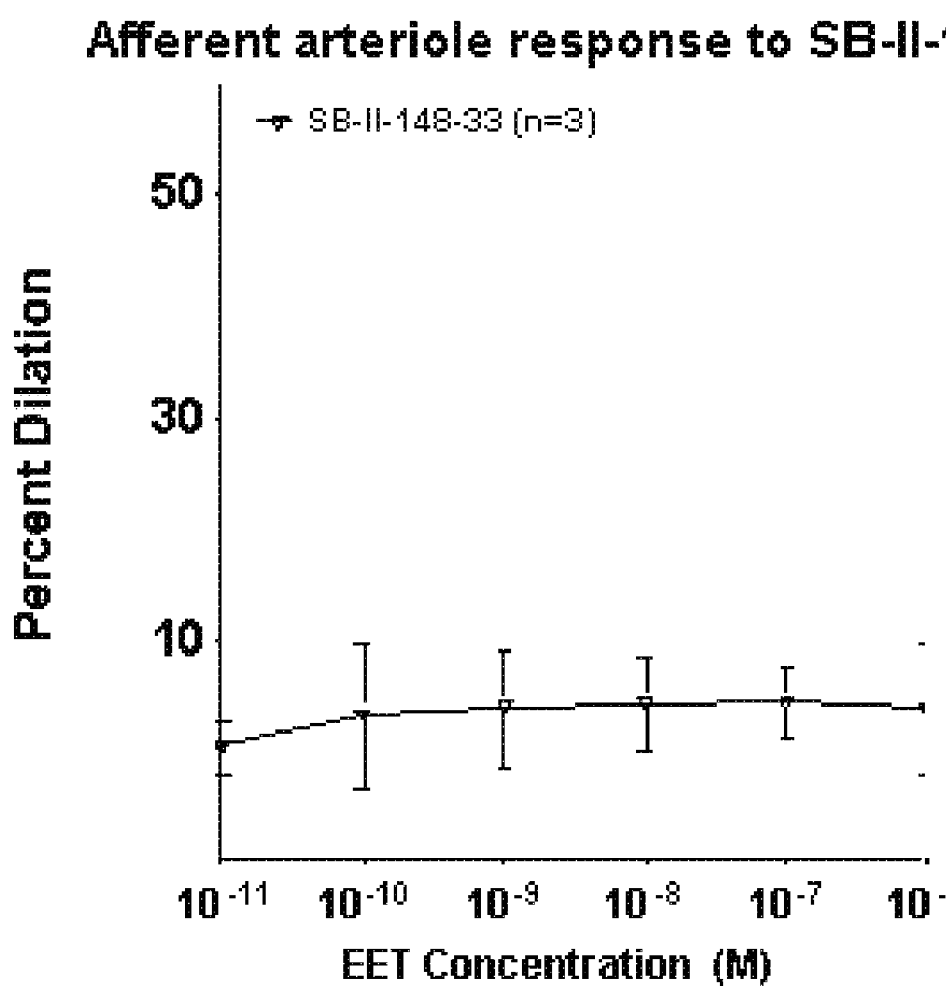
Figure 2:
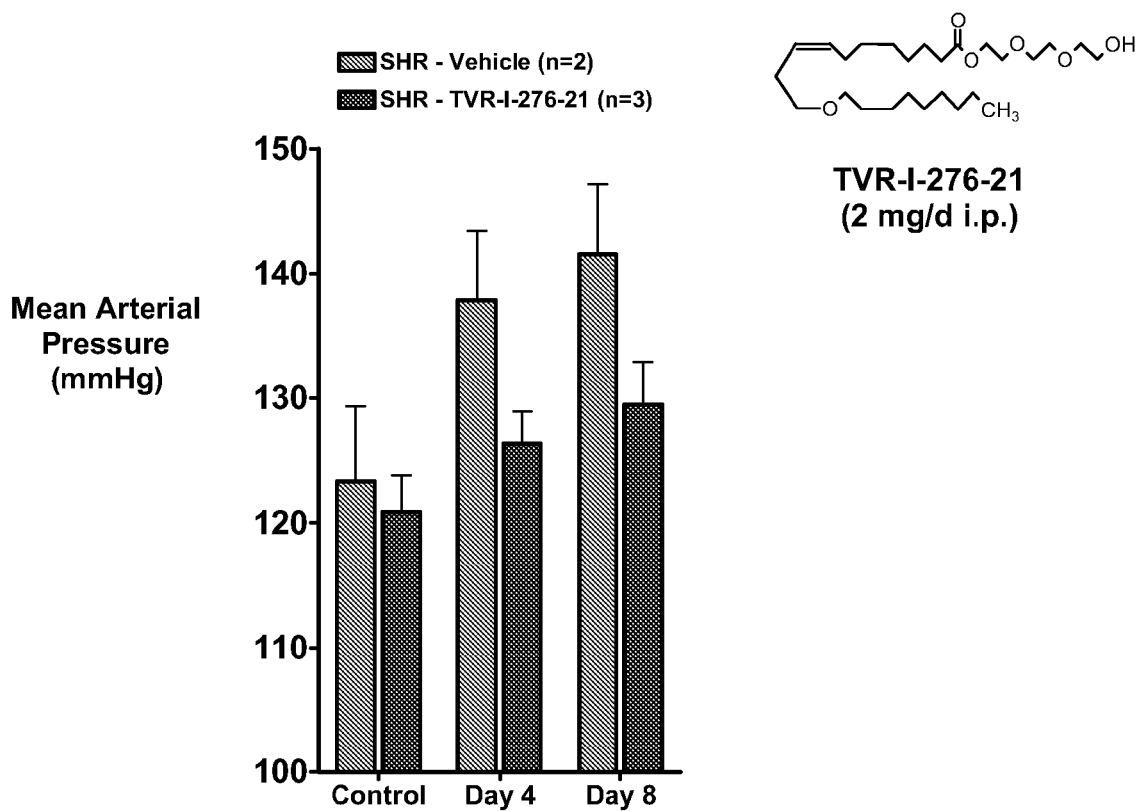
FIG. 2 shows the effect of the 11-nonyloxy-undec-8(Z)-enoic acid derivative TVR-I-276-21 on the mean arteriole pressure in spontaneously hypertensive rats (SHRs) as compared to the effect of vehicle alone. The chemical structure of the compound tested is shown above the graph. The effect of the compound is shown in the bar graph, and is represented as the mean arteriole pressure (mmHg).

The present invention may be understood more readily by reference to the following detailed description of the preferred embodiments of the invention and the Examples included herein. However, before the present methods are disclosed and described, it is to be understood that this invention is not limited to the specific compounds, specific compositions, specific conditions, or specific methods, etc., as such may, of course, vary, and the numerous modifications and variations therein will be apparent to those skilled in the art. it is also to be understood that the terminology used herein is for the purpose of describing specific embodiments only and is not intended to be limiting. It is further to be understood that unless specifically defined herein, the terminology used herein is to be given its traditional meaning as known in the relative art.

As used in the specification and the appended claims, the singular forms "a," "an," and "the" include plural forms unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The present invention describes for the first time that the disclosed epoxide metabolite derivatives are useful to increase renal blood flow and to promote sodium secretion. It has been proposed that the epoxide metabolite EETs are the endothelium-derived hyperpolarizing factors (EDHFs). Additionally, EETs have been demonstrated to have profibrinolytic effects, to have anti-inflammatory actions, and to inhibit smooth vascular muscle cell migration.

The invention provides compounds that are derivatives of 11-nonyloxy-undec-8(Z)-conic acid or a pharmaceutically acceptable salt thereof, wherein the compound reduces blood pressure. In a preferred embodiment, the compound has the structural formula:

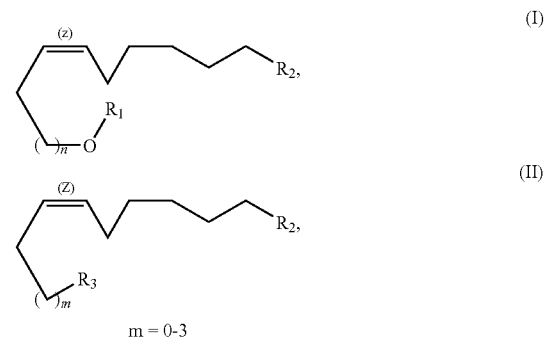

or a pharmaceutically acceptable salt thereof, wherein
n is 1 to 4; m is 0 to 3
$R_1$ is selected from the group consisting of a linear or branched alkyl and cycloalkyl, each having up to 10 carbon atoms;
$R_2$, in each occurrence, is selected from the group consisting of linear or branched alkyl, cycloalkyl, alkyloxy, alkylthio, alkylamino, alkenyl, alkoxycarbonyl, carboxyalkylamide, thiazolidinyl-2,4-dione, or heterocyclyl, each optionally substituted with one or more halogen, OH, $CO_2H$, $NH_2$, alkoxy, alkylamine, $NO_2$, $SO_3$alkyl, alkylthio, alkylsulfinyl, or alkylsulfonyl, and each having up to 12 carbon atoms; and
$R_3$ is a $C_{6-9}$ epoxide. In certain embodiments, $R_2$ is selected from the group consisting of:

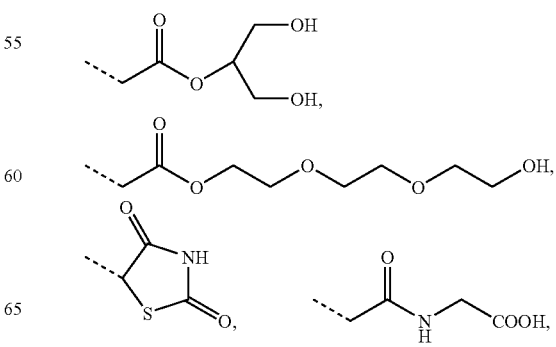

-continued

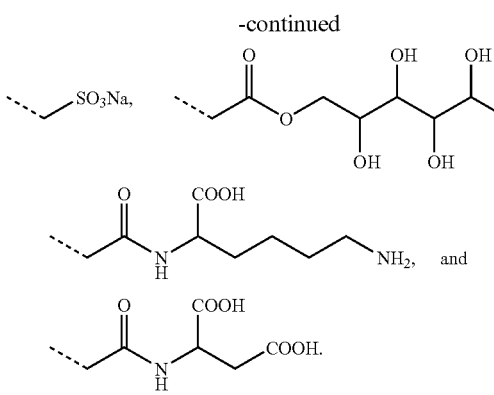

In another preferred embodiment the compound is selected from the group consisting of:

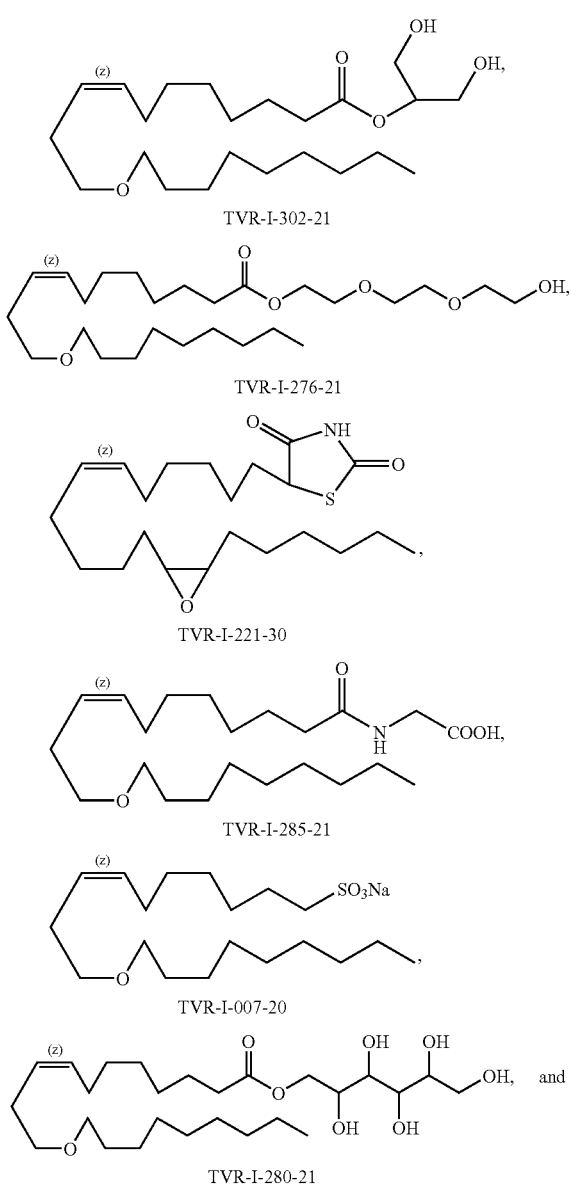

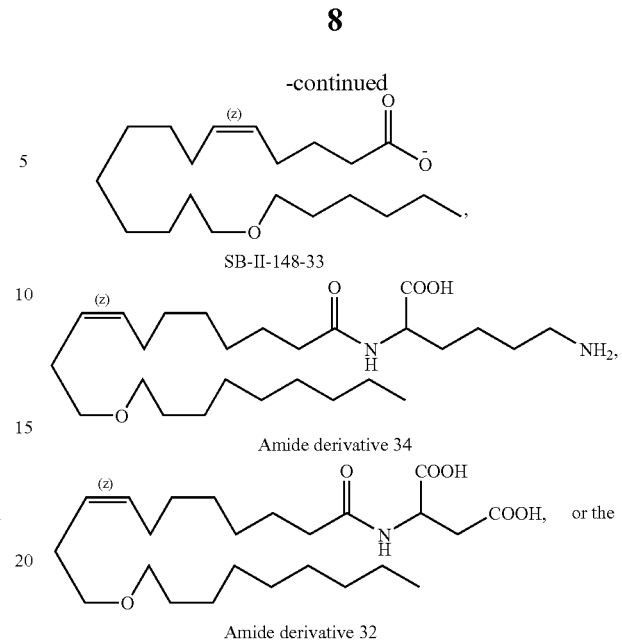

pharmaceutically acceptable salts or derivatives thereof.

Any of the compounds of formula I or II containing one or more asymmetric carbon atoms may occur as racemates and racemic mixtures, single enantiomers, diastereomeric mixtures, or individual diastereomers. All such isomeric forms of these compounds are expressly included in the present invention. Each stereogenic carbon may be in the R or S configuration, or a combination of configurations. Some of the compounds of formula I or II can exist in more than one tautomeric form. The invention includes use of all such tautomers.

The compounds of formula I and II are only those which are contemplated to be "chemically stable" as will be appreciated by those skilled in the art. For example, compounds which would have a "dangling valency," or a "carbanion" are not compounds contemplated to be used in the methods of the invention.

All alkyl, alkylene, alkenyl, alkenylene, alkynyl, and alkynylene groups shall be understood as being $C_{1-12}$, branched or unbranched unless otherwise specified. As used herein, the phrase "pharmaceutically acceptable salt or derivative" includes any pharmaceutically acceptable salt or ester of a compound of this invention, or any other compound which, upon administration to a patient, is capable of providing (directly or indirectly) a compound used in this invention, a pharmacologically active metabolite, or pharmacologically active residue thereof.

The present invention also provides pharmaceutical compositions comprising a therapeutically effective amount of a compound that is a derivative of 11-nonyloxy-undec-8(Z)-eonic acid or a pharmaceutically acceptable salt thereof, wherein the compound reduces blood pressure. In a preferred embodiment, the compound has the structural formula.

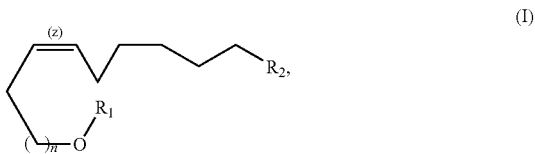

(I)

-continued

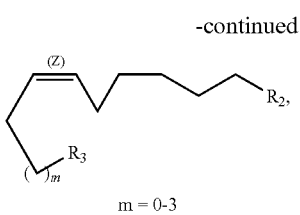

(II)

m = 0-3 or a pharmaceutically acceptable salt thereof, wherein
n is 1 to 4; m is o to 3;
R$_1$ is selected from the group consisting of a linear or branched alkyl and cycloalkyl, each having up to 10 carbon atoms;
R$_2$, in each occurrence, is selected from the group consisting of linear or branched alkyl, cycloalkyl, alkyloxy, alkylthio, alkylamino, alkenyl, alkoxycarbonyl, carboxyalkylamide, thiazolidinyl-2,4-dione, or heterocyclyl, each optionally substituted with one or more halogen, OH, CO$_2$H, NH$_2$, alkoxy, alkylamine, NO$_2$, SO$_3$alkyl, alkylthio, alkylsulfinyl, or alkylsulfonyl, and each having up to 12 carbon atoms; and
R$_3$ is a C$_{6-9}$ epoxide. In certain embodiments, R$_2$ is selected from the group consisting of:

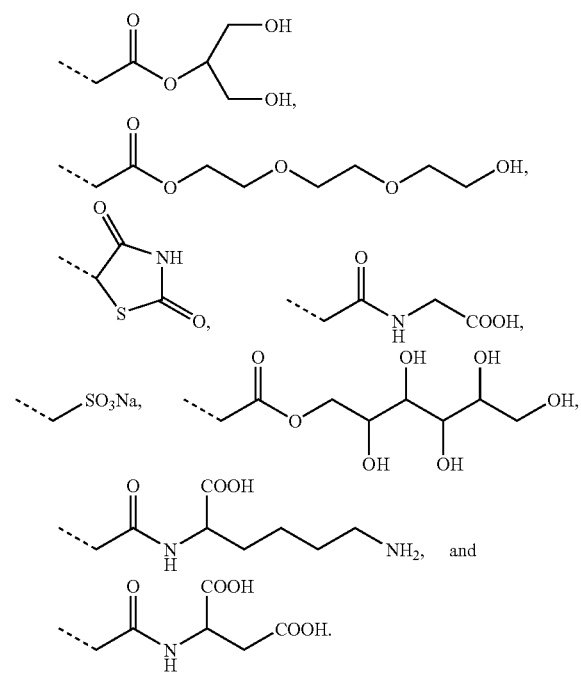

In another preferred embodiment, the pharmaceutical compositions of the present invention comprise a therapeutically effective amount of a compound selected from the group consisting of:
(Z)-1,3-dihydroxypropan-2-yl 11-(nonyloxy)undec-8-enoate,
(Z)-2-(2-(2-hydroxyethoxy)ethoxy)ethyl 11-(nonyloxy)undec-8-enoate,
(Z)-2-(11-(nonyloxy)undec-8-enamido)acetic acid,
sodium (Z)-10-(nonyloxy)dec-7-ene-1-sulfonate,
(Z)-2,3,4,5,6-pentahydroxyhexyl 11-(nonyloxy)undec-8-enoate,
(Z)-5-(11-(3-hexyloxiran-2-yl)undec-6-enyl)thiazolidine-2,4-dione,
(Z)-14-(hexyloxy)tetradec-5-enoate,
(Z)-6amino-2-(11-(nonyloxy)undec-8-enamido)hexanoic acid, and
(Z)-2-(11-(nonyloxy)undec-8-enamido)succinic acid.

The present invention also provides methods for treating a renal or cardiovascular disease, said method comprising administering to a patient in need thereof a therapeutically effective amount of a compound that is a derivative of 11-nonyloxy-undec-8(Z)-eonic acid or a pharmaceutically acceptable salt thereof, wherein the compound reduces blood pressure. In a preferred embodiment, the compound has the structural formula:

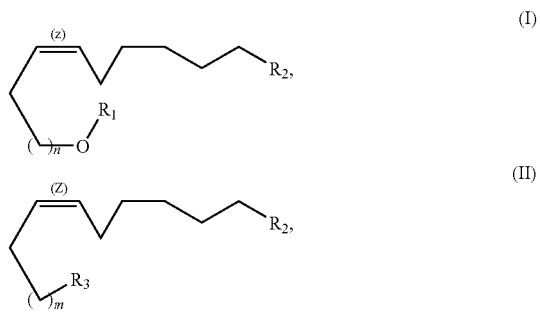

m = 0-3 or a pharmaceutically acceptable salt thereof, wherein
n is 1 to 4; m is 0 to 3;
R$_1$ is selected from the group consisting of a linear or branched alkyl and cycloalkyl, each having up to 10 carbon atoms;
R$_2$, in each occurrence, is selected from the group consisting of linear or branched alkyl, cycloalkyl, alkyloxy, alkylthio, alkylamino, alkenyl, alkoxycarbonyl, carboxyalkylarnide, thiazolidinyl-2,4-dione, or heterocyclyl, each optionally substituted with one or more halogen, OH, CO$_2$H, NH$_2$, alkoxy, alkylamine, NO$_2$, SO$_3$alkyl, alkylthio, alkylsulfinyl, or alkylsulfonyl, and each having up to 12 carbon atoms; and
R$_3$ is a C$_{6-9}$ epoxide. In certain embodiments, R$_2$ is selected from the group consisting of:

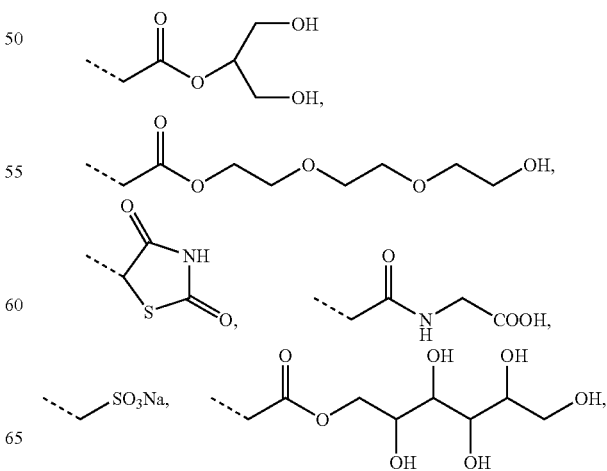

-continued

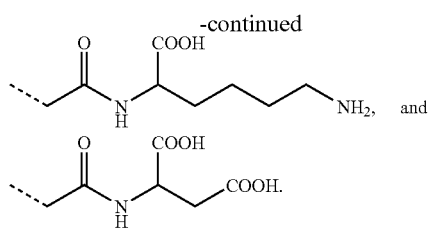

In another preferred embodiment, the methods for treating a renal or cardiovascular disease comprises administering to a patient in need thereof a therapeutically effective amount of a compound selected from the group consisting of:
(Z)-1,3-dihydroxypropan-2-yl 11-(nonyloxy)undec-8-enoate,
(Z)-2-(2-(2-hydroxyethoxy)ethoxy)ethyl 11-(nonyloxy)undec-8-enoate,
(Z)-2-(11-(nonyloxy)undec-8-enamido)acetic acid,
sodium (Z)-10-(nonyloxy)dec-7-ene-1-sulfonate,
(Z)-2,3,4,5,6-pentahydroxyhexyl 11-(nonyloxy)undec-8-enoate,
(Z)-5-(11-(3-hexyloxiran-2-yl)undec-6-enyl)thiazolidine-2,4-dione,
(Z)-14-(hexyloxy)tetradec-5-enoate,
(Z)-6-amino-2-(11-(nonyloxy)undec-8-enamido)hexanoic acid, and
(Z)-2-(11-(nonyloxy)undec-8-enamido)succinic acid.

In certain preferred embodiments of the present invention, the methods for treating renal or cardiovascular disease are used to treat a patient with a disease or condition selected from a group consisting of but not limited to, type 1 and type 2 diabetes, heptorenal syndrome, metabolic syndrome, insulin resistance syndrome, glomerulonephritis, hypertension, congestive heart failure, heart attack, hypertensive heart disease, atherosclerosis, coronary artery disease, angina, ischemia, ischemic stroke, Raynaud's disease, and renal disease.

In certain other embodiments of the present invention, the methods further comprise administering to the patient a therapeutically effective amount of an additional agent that is used to treat renal and/or cardiovascular disease. As used herein, a "therapeutically effective amount" is an amount which increases renal blood flow, promotes sodium secretion, has a profibrinolytic effect, has an anti-inflammatory effect, and/or inhibits smooth vascular muscle cell migration. As also used herein, an "additional agent that is used to treat renal and/or cardiovascular disease" refers to a molecule which increases renal blood flow, promotes sodium secretion, has a profibrinolytic effect, has an anti-inflammatory effect, and/or inhibits smooth vascular muscle cell migration. In certain embodiments, the additional agent is selected from the group consisting of alpha blockers, angiotensin-converting enzyme (ACE) inhibitors, angiotensin receptor blockers (ARBs), beta-blockers, calcium channel blockers, central alpha agonists, diuretics, renin inhibitors, including aliskiren, vasodilators, clonidine, diazoxide, furosemide, hydralazine, minoxidil, and nitroprusside.

Another aspect of the invention pertains to the use of isolated epoxide derivative compounds. An "isolated" or "purified" epoxide derivative compound or biologically active portion thereof is "substantially free of chemical precursors or other chemicals." This includes preparations of the epoxide derivative compound in which the compound is separated from chemical precursors or other chemicals that are involved in the synthesis of the derivative compound. In one embodiment, the language "substantially free of chemical precursors or other chemicals" includes preparations of an epoxide derivative having less than about 30% (by dry weight) of chemical precursors or other chemicals, more preferably less than about 20% chemical precursors or other chemicals, still more preferably less than about 10% chemical precursors or other chemicals, and most preferably less than about 5% chemical precursors or other chemicals.

The compositions of this invention further comprise a pharmaceutically acceptable carrier. The phrases "pharmaceutically or pharmacologically acceptable" refer to molecular entities and compositions that do not produce an adverse, allergic, or other untoward reaction when administered to an animal, or a human, as appropriate. Veterinary uses are equally included within the invention and "pharmaceutically acceptable" formulations include formulations for both clinical and/or veterinary use. As used herein, "pharmaceutically acceptable carrier" includes any and all solvents, dispersion media, coatings, antibacterial, and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. For human administration, preparations should meet sterility, pyrogenicity, and general safety and purity standards as required by FDA Office of Biologics standards. Supplementary active ingredients can also be incorporated into the compositions.

As used herein with respect to these methods, the term "administering" refers to various means of introducing a composition into a cell or into a patient. These means are well known in the art and may include, for example, injection; tablets, pills, capsules, or other solids for oral administration; nasal solutions or sprays; aerosols, inhalants; topical formulations; liposomal forms; and the like. As used herein, the term "effective amount" or "therapeutically effective amount" refers to an amount that will result in the desired effect and may readily be determined by one of ordinary skill in the art.

The compositions of the present invention may be formulated for various means of administration. As used herein, the term "route" of administration is intended to include, but is not limited to subcutaneous injection, intravenous injection, intraocular injection, intradermnal injection, intramuscular injection, intraperitoneal injection, intratracheal administration, epidural administration, inhalation, intranasal administration, oral administration, sublingual administration, buccal administration, rectal administration, vaginal administration, and topical administration. The preparation of an aqueous composition that contains the desired epoxide metabolite derivative compound as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The compositions of the present invention can be formulated into a sterile aqueous composition in a neutral or salt form. Solutions as free base or pharmacologically acceptable salts can be prepared in water suitably mixed with a surfactant, such as hydroxypropylcellulose. "Pharmaceutically acceptable salts" include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate, and gelatin.

Prior to or upon formulation, the compositions of the present invention should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filter sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the active compound admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and purity standards as required by FDA Office of Biological Standards.

Throughout this application and the priority application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

For any particular compound disclosed herein, the general structure presented is also intended to encompasses all conformational isomers and stereoisomers that may arise from a particular set of substituents, unless indicated otherwise. Thus, the general structure encompasses all enantiomers, diastereomers, and other optical isomers whether in enantiomeric or racemic forms, as well as mixtures of stereoisomers, as the context permits or requires.

Compound names were generated from the structures illustrated herein, using the structure-to-name conversion tool of ChemDraw Ultra (Version 10.0, c. 1986-2005, CambridgeSoft) and are not intended to contradict the structure. Therefore, the structure provided is intended to be controlling.

Also unless indicated otherwise, when a range of any type is disclosed or claimed, for example a range of carbon atoms, molecular weights, activities, concentrations, temperatures, and the like, it is intended to disclose or claim individually each possible number that such a range could reasonably encompass, including any sub-ranges encompassed therein. For example, when the Applicants disclose or claim a chemical moiety having a certain number of atoms, for example carbon atoms, Applicants' intent is to disclose or claim individually every possible number that such a range could encompass, consistent with the disclosure herein. Thus, by the disclosure that an alkyl substituent or group can have from 1 to 10 carbon atoms or "up to" 10 carbon atoms, Applicants intent is to recite that the alkyl group have 1, 2, 3, 4, 5, 6, 7, 8, 9, or 10 carbon atoms, including any ranges, sub-ranges, or combinations thereof between any number of carbon atoms recited herein. Accordingly, Applicants reserve the right to proviso out or exclude any individual members of such a group, including any sub-ranges or combinations of sub-ranges within the group, that can be claimed according to a range or in any similar manner, if for any reason Applicants choose to claim less than the full measure of the disclosure.

All publications and patents mentioned in the disclosure of this invention are incorporated herein by reference in their entireties, for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention. Should the usage or terminology used in any reference that is incorporated by reference conflict with the usage or terminology used in this disclosure, the usage and terminology of this disclosure controls.

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

In the following examples, unless otherwise specified, solvents were purchased from commercial sources and were typically dried prior to use. Unless otherwise specified, reagents were obtained from commercial sources.

Example 1

Synthesis of 11-nonyloxy-8(Z)-enoic Acid and Derivatives

The compound 11-nonyloxy-8(Z)-enoic acid (Ether-EET) was synthesized as described previously (Falck et al., 2003, Bioorg. Med. Chem. Lett. 13:4011-14)(See below),

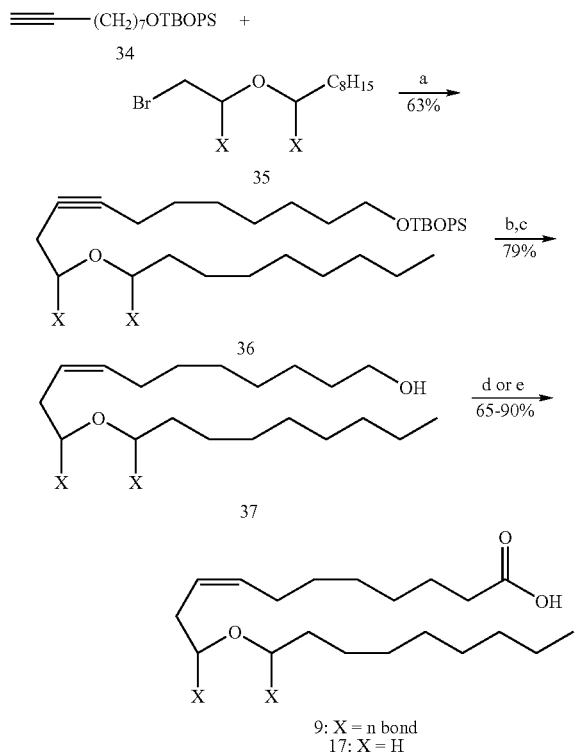

The Ether-EET analogue was synthesized: (a) n-BuLi, THF/HMPA (4:1), −40° C., 2 hours; bromide, −40° C. to room temperature, 2 hours; (b) n-Bu$_4$NF, THF, 0° C., 4 hours; (c) P-2 Ni/H$_2$, EtOH, room temperature, 2 hours; (d) PDC, DMF, room temperature, 16 hours; (e) Jones reagent, acetone, −20° C., 4 hours.

The chemical synthesis of Ether-EET as shown above is indicative of the approach used for the seven 11-nonyloxy-8 (Z)-enoic acid derivatives ((Z)-1,3-dihdroxypropan-2-yl 11-(nonyloxy)undec-8-enoate (TVR-I-302-21), (Z)-2-(2-(2-hydroxyethoxy)ethoxy)ethyl 11-(nonyloxy)undec-8-enoate (TVR-I-276-21), (Z)-2-(11-(nonyloxy)undec-8-enamido) acetic acid (TVR-I-221-30), (Z)-(10-(nonyloxy)dec-7-ene-1-sulfonate (TVR-I-285-21), (Z)-2,3,4,5,6-pentahydroxyhexyl 11-(nonyloxy)undec-8-enoate (TVR-II-007-20), (Z)-5-(11-(3-hexyl oxiran-2-yl)undec-6-enyl)thiazolidine-2,4-dione (TVR-I-280-21), (Z)-14-(hexyloxy)tetradec-5-enoate (SB-II-148-33). The specific methods of chemical synthesis are shown below.

Synthesis of Glyceryl Ester Derivative 4 ((Z)-1,3-dihdroxypropan-2-yl 11-(nonyloxy undec-8-enoate (TVR-I-302-21)

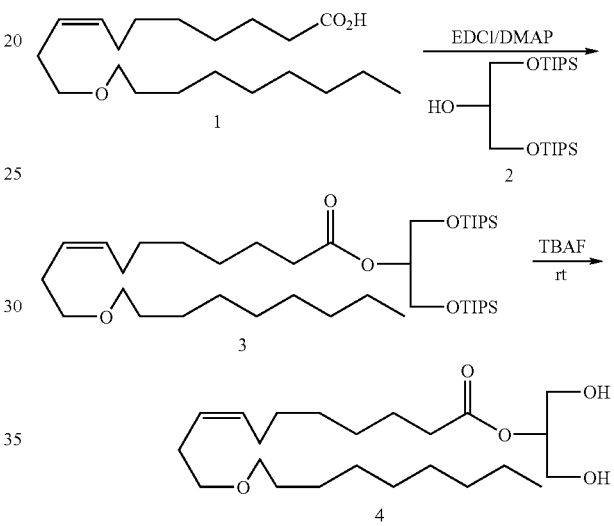

The synthesis of the glyceryl ester derivative 4 ((Z)-1,3-dihdroxypropan-2-yl 11-(nonyloxy)undec-8-enoate (TVR-I-302-21)) is shown above. A mixture of acid 1 (100 mg, 0.31 mmol)(Falck et al., 2003 Bioorg. Med. Chem. Lett. 13:4011-14) and 1,3-di(triisopropylsilyl)glycerol 2 (136 mg, 0,34 mmol)(Han & Razdan, 1999, Tetrahedron Lett. 40:1631-34) was dried under vacuum (<1 mmHg) for 1 hour. DMAP (45 mg, 0.37 mmol) and 1-[3-(dimethylamino)propyl]-3-ethylcarbodiimide hydrochloride (70 mg, 0.37 mmol) were added to the above, and the whole was dried again for 1 hour under vacuum. Dry dichloromethane (6 mL) was added to this mixture, and the resultant solution was stirred overnight at room temperature. The reaction mixture was then diluted with more dichloromethane (25 mL), washed sequentially with water (2×20 mL) and brine (10 mL), dried over Na$_2$SO$_4$, and concentrated under reduced pressure. The residue which was purified by SiO$_2$ flash column chromatography using 2% EtOAc/hexanes as eluent to furnish the glyceride 3 (180 mg, 82%). TLC: 10% ethyl acetate/hexanes, R$_f$~0.9; $^1$H NMR (CDCl$_3$, 300 MHz) δ 5.50-5.30 (m, 2H), 4.90 (apparent quintet, 1H, J=5.2 Hz), 3.90-3.78 (m, 4H), 3.40 (t, 2H, J=6.7 Hz), 3.39 (t, 2H, J=7.3 Hz), 2.31 (apparent q, 2H, J=6.7 Hz), 2.29 (t, 2H, J=7.3 Hz), 2.03 (apparent q, 2H, J=6.4 Hz), 1.66-1.50 (m, 6H), 1.40-1.24 (m, 14H), 1.18-1.00 (m, 44H), 0.87 (t, 3H, J=6.4 Hz).

A soultion of tetra-n-butylammonium fluoride (0.64 mL, 0.64 mmol, 1M in THF) was added to a solution of 3 (180 mg, 0.25 mmol) in dry THF (6 mL) at 0° C. under an argon atmosphere. After stirring for 6 hours, ether (100 mL) was added to the reaction mixture which was then washed sequentially with water (2×30 mL) and brine (20 mL), dried over Na$_2$SO$_4$, and concentrated under reduced pressure to give a residue that was purified by SiO$_2$ flash chromatography using 40% EtOAc/hexanes as eluent to furnish 4 (98 mg, 96%) as a colorless oil. TLC: 50% EtOAc/hexanes, R$_f$~0.2; $^1$H NMR (CDCl$_3$, 300 MHz) δ 5.56-5.30 (m, 2H), 4.24-4.11 (m, 2H), 3.97-3.89 (m, 1H), 3.69 (dd, 1H, J=4.0, 11.3 Hz), 3.59 (dd, 1H, J=5.8, 11.3 Hz), 3.41 (t, 2H, J=7.0 Hz), 3.40 (t, 2H, J=7.0 Hz), 2.41-2.25 (m, 4H), 2.04 (q, 2H, J=6.4, 6.7 Hz), 1.70-1.52 (m, 4H), 1.40-1.16 (m, 18H), 0.88 (t, 3H, J=6.4 Hz).

Synthesis of PEG Ester Derivative 5 ((Z)-2-(2-(2-hydroxyethoxy)ethoxy)ethyl 11-(nonyloxy) undec-8-enoate TVR-I-276-21)

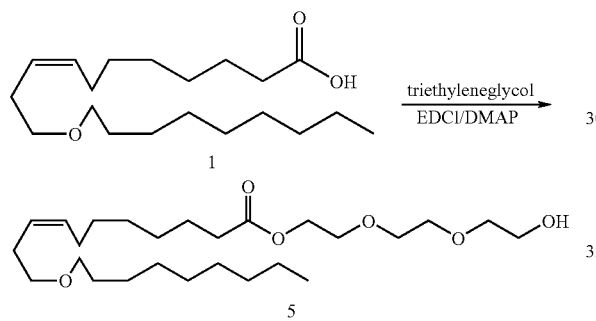

The synthesis of the PEG Ester Derivative 5 ((Z)-2-(2-(2-hydroxyethoxy)ethoxy)ethyl 11-(nonyloxy) undec-8-enoate (TVR-I-276-21) is shown above. A mixture of 1 (125 mg, 0.38 mmol) and triethyleneglycol (574 mg, 3.83 mmol) was dried under vacuum (<1 mmHg) for 1 h. To this were added N,N-dimethylaminopyridine (56 mg, 0.46 mmol) and 1-[3-(dimethylamino)propyl]-3-ethylcarbodiimide hydrochloride (EDCI, 88 mg, 0.46 mmol), and the whole was dried again under vacuum for another 1 hour. The above mixture was dissolved in dry dichloromethane (5 mL) under an argon atmosphere. After stirring overnight at room temperature, all volatiles were evaporated in vacuo, and the residue was purified by SiO$_2$ flash column chromatography using 30% EtOAc/hexanes as eluent to furnish PEG ester 5 (150 mg, 86%). TLC: 50% EtOAc/hexanes, R$_f$~0.24; $^1$H NMR (CDCl$_3$, 400 MHz) δ 5.48-5.32 (m, 2H), 4.24 (t, 2H, J=4.7 Hz), 3.76-3.60 (m, 10H), 3.41 (t, 2H, J=6.7 Hz), 3.39 (t, 2H, J=7.0 Hz), 2.33 (t, 2H, J=7.6 Hz), 2.31 (apparent q, 2H, J=5.8 Hz), 2.03 (apparent q, 2H, J=6.7 Hz), 1.68-1.52 (m, 4H), 1.40-1.20 (m, 18H), 0.88 (t, 3H, J=6.4 Hz); $^{13}$C NMR (CDCl$_3$, 75 MHz) δ 173.59, 131.50, 125.43, 72.38, 70.82, 70.36, 70.26, 70.14, 69.00, 63.03, 61.48, 33.93, 31.70, 29.55, 29.38, 29.32, 29.24, 29.09, 28,82, 28.70, 27.78, 27.05, 25.98, 24.64, 22.48, 13.93.

Synthesis of 2,4-Thiazolidinedione Derivative ((Z)-2-(11-(nonyloxy)undec-8-enamido)acetic acid TVR-I-221-30)

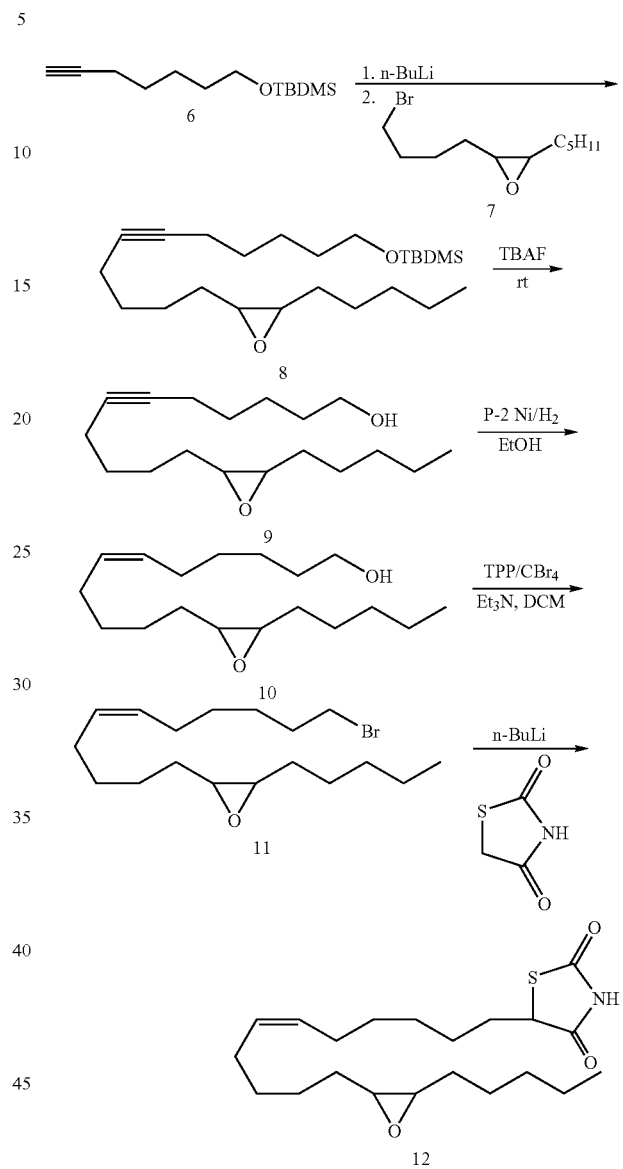

The synthesis of the 2,4-Thiazolidinedione Derivative 12 ((Z)-2-(11-(nonyloxy)undec-8-enamido)acetic acid (TVR-I-221-30)) is shown above. n-Butyl lithium (Aldrich, 2.5 M in hexanes, 1.93 mL, 4.62 mmol) was added dropwise to a −78° C. solution of 6 (0.95 g, 3.85 mmol)(Kanbe et al., 2006, P., Bioorg. Med. Chem. Lett. 16:4090-94) in a mixture of anhydrous THF:HMPA (4:1, 12 mL) under an argon atmosphere. After stirring for 30 minutes at −78° C. and then at room temperature for 2 hours, the reaction mixture was re-cooled to −78° C. Into this was slowly cannulated a solution of 2-(4-bromo-butyl)-3-pentyl-oxirane (7) (0.80 g, 3.21 mmol) (Falck et al., 2003, Am. J. Physiol. 284:11337-49) in dry THF (4 mL) with stirring. After 1 hour at −78° C., the reaction mixture was gradually warmed to room temperature. After stirring overnight, the reaction mixture was re-cooled to ° C., quenched with saturated aq. ammonium chloride, acidified to pH 4 with aq. oxalic acid solution (1M), and extracted with ether (3×60 mL). The combined ethereal extracts were washed with water (3×30 mL), brine (2×30 mL), dried over Na₂SO₄, and concentrated under reduced pressure. The residue which was purified by SiO₂ flash chromatography using 10% EtOAc/hexanes to furnish 8 (0.80 g, 60%) as a colorless oil. TLC: 20% ethyl acetate/hexanes, $R_f$~0.72; ¹H NMR (CDCl₃, 400 MHz) δ 3.72 (t, 2H, J=6.7 Hz), 2.86-2.78 (m, 2H), 2.46-2.38 (m, 4H), 1.62-1.22 (m, 20H), 0.98 (s, 9H), 0.87(t, 3H, J=6.9 Hz), 0.25 (s, 6H).

A solution of tetra-n-butylammonium fluoride (Aldrich, 1M in THF, 3.8 mL, 3.86 mmol) was added to a 0° C. solution of 8 (0.80 g, 1.93 mmol) in dry THF (15 mL) under an argon atmosphere. After 2 hours, the reaction mixture was diluted with ether (100 mL), and the mixture was washed with water (2×30 mL), brine (20 mL), dried over Na₂SO₄, and concentrated under reduced pressure. The residue was purified by SiO₂ flash chromatography eluting with 20% EtOAc/hexanes to furnish alcohol 9 (0.46 g, 80%) as a colorless oil. TLC: 30% ethyl acetate/hexanes, $R_f$~0.46; ¹H NMR (CDCl₃, 400 MHz) δ 3.64 (t, 2H, J=6.4 Hz), 2.96-2.89 (m, 2H), 2.13-2.22 (m, 4H), 1.66-1.30 (m, 20H), 0.90 (t, 3H, J=6.4 Hz).

NaBH₄ (14 mg, 0.39 mmol) was added with stirring to a solution of Ni(OAc)₂ (98 mg, 0.39 mmol) in absolute ethanol (2 mL). After stirring for 15 minutes under a H₂ atmosphere (1 atm), freshly distilled ethylenediamine (EDA, 47 μL, 0.78 mmol) was added. After another 15 minutes, a solution of 9 (0.46 g, 1.57 mmol) in absolute ethanol (2 mL) was added. Following an additional 3 hours at room temperature, the reaction mixture was diluted with ether (10 mL), filtered through a small bed of silica gel, and concentrated under reduced pressure. The residue was purified by SiO₂ flash chromatography using 30% EtOAc/hexanes to furnish cis-olefin 10 (0.45 g, 96%). TLC: 30% EtOAc/hexanes, $R_f$~0.45; ¹H NMR (CDCl₃, 400 MHz) δ 5.41-5.32 (m, 2H), 3.64 (t, 2H, J=6.4 Hz), 2.92-2.84 (m, 2H), 2.10-2.00 (m, 4H), 1.65-1.30 (m, 20H), 0.90 (t, 3H, J=7.1 Hz).

Triethylamine (0.21 mL, 1.51 mmol) was added to a 0° C. solution of 10 (0.44 g, 1.51 mmol) in dry dichloromethane (10 mL) under an argon atmosphere followed sequentially by carbon tetrabromide (0.60 g, 1.81 mmol) and triphenylphosphine (0.47 g, 1.81 mmol). After stirring at 0° C. for 8 hours, all volatiles were evaporated using a rotavapor. The residue was purified by SiO₂ flash chromatography with 5% EtOAc/hexanes to furnish bromide 11 (0.41 g, 74%). TLC: 20% EtOAc/hexanes, $R_f$~0.83; ¹H NMR (CDCl₃, 400 MHz) δ 5.43-5.31 (m, 2H), 3.40 (t, 2H, J=6.7 Hz), 2.93-2.88 (m, 2H), 1.91-1.86 (m, 4H), 1.56-1.29 (m, 20H), 0.90 (t, 3H, J=7.1 Hz); ¹³C NMR (CDCl₃, 75 MHz) δ 130.00, 129.78, 57.37, 57.28, 34.02, 32.88, 31.89, 29.73, 28.99, 27.97, 27.95, 27.90, 27.28, 27.15, 26.45, 26.41, 22.76, 14.17.

n-BuLi (Aldrich., 2.5 M in hexanes, 0.5 mL, 1.20 mmol) was added dropwise to a −78° C. solution of 2,4-thiazolidinedione (Aldrich, 59 mg, 0.50 mmol) in dry THF/HMPA (4:1, 10 mL) under an argon atmosphere. After stirring for 30 minutes at the same temperature and then at 0° C. for 1 hour, the reaction mixture was re-cooled to −78° C., and a solution of 11 (150 mg, 0.42 mmol) in dry THF (5 mL) was added dropwise. The reaction mixture was slowly warmed to room temperature over 3 hours and kept at this temperature for a further 12 hours. The reaction was then quenched by the addition of saturated aq. NH₄Cl (5 mL) and extracted into EtOAc (2×30 mL). The combined organic extracts were washed with water (2×10 mL), brine (10 mL), dried over anhydrous Na₂SO₄, and concentrated in vacuo. The residue was purified by column chromatography to afford 12 (50 mg, 30%). TLC: 30% EtOAc/hexanes, $R_f$~0.48; ¹H NMR (CDCl₃, 400 MHz) δ 9.20-8.80 (br s, 1H), 5.41-5.30 (m, 2H), 4.31-4.24 (m, 1H), 2.96-2.91 (m, 2H), 2.20-1.87 (m, 6H), 1.57-1.25 (m, 20H), 0.90 (t, J=6.9 Hz, 3H); ¹³C NMR (CDCl₃, 75 MHz) δ 175.72, 171.42, 130.0, 129.78, 57.70, 57.59, 57.54, 32.82, 31.86, 29.71, 29.35, 28.59, 28.57, 27.79, 27.29, 27.05, 27.02, 26.79, 26.73, 26.39, 14.16; IR (neat) 2933, 2857, 1756, 1704, 3186 cm⁻¹; ESMS m/z 404 (M+Na).

Synthesis of Mannitol Ester Derivative 13 ((Z)-5-(11-(3-hexyl oxiran-2-yl)undec-6-enyl)thiazolidine-2,4-dione (TVR-I-280-21))

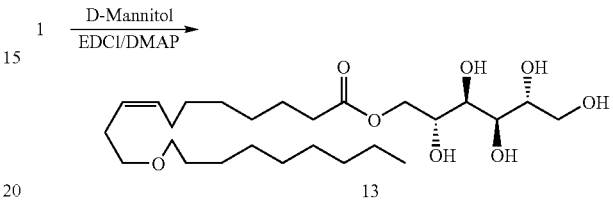

The synthesis of the Mannitol Ester Derivative 13 ((Z)-5-(11-(3-hexyl oxiran-2-yl)undec-6-enyl)thiazolidine-2,4-dione (TVR-I-280-21)) is shown above. A mixture of 1 (125 mg, 0.38 mmol)(Falck et al., 2003, Bioorg. Med. Chem. Lett. 13:4011-14) and D-mannitol (140 mg, 0.76 mmol) were dried under vacuum (<1 mmHg) for 1 hour. To this were added N,N-dimethylaminopyridine (DMAP, 56 mg, 0.46 mmol) and 1-[3-(dimethylamino) propyl]-3-ethylcarbodiimide hydrochloride (EDCI, 88 mg, 0.46 mmol), and the whole was dried again under vacuum for another 1 hour. This mixture was dissolved in dry DMF (3 mL) and stirred under an argon atmosphere. After stirring overnight, all volatiles were evaporated in vacuo and the residue was purified by PTLC using hexanes/ethyl acetate/methanol (4:1:0.6) as eluent to furnish ester 13 (152 mg, 81%). TLC. hexanes/ethyl acetate/methanol (4:1:0.6), $R_f$~0.54; ¹H NMR (CDCl₃, 300 MHz) δ 5.52-5.28 (m, 2H), 4.37 (dd, 1H, J=2, 11 Hz), 4.15 (dd, 1H, J=6, 11 Hz), 3.92-3.58 (m, 6H), 3.48-3.36 (m, 4H) 2.40-2.24 (m, 4H), 2.10-2.00 (m, 2H), 1.70-1.48 (m, 4H), 1.44-1.24 (m, 18H), 0.89 (t, 3H, J=7 Hz).

Synthesis of Glycine Amide Derivative 15 ((Z)-(10-(nonyloxy)dec-7-ene-1-sulfonate (TVR-I-285-21))

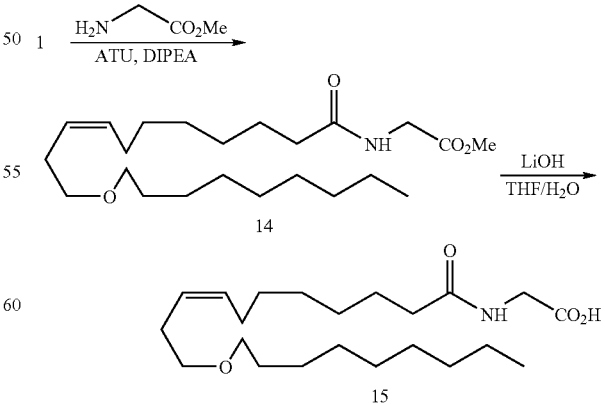

The synthesis of the Glycine Amide Derivative 15 ((Z)-(10-(nonyloxy)dec-7-ene-1-sulfonate (TVR-I-285-21)) is shown above. O-(7-Azabenzotriazol-1-yl)-N,N,N',N'-tetramethyluronium hexafluorophosphate (ATU, 160 mg, 0.42 mmol) was added to a solution of acid 1 (125 mg, 0.38 mmol)(Falck et al., 2003, Bioorg. Med. Chem. Lett. 13:4011-14) in dry DMF (2 mL). After stirring for 15 minutes, glycine methyl ester (58 mg, 0.46 mmol) and N,N-diisopropylethylamine (60 μL, 0.46 mmol) in dry DMF (2 mL) were added to the above at room temperature. After stirring overnight, the reaction mixture was diluted with ethyl acetate (40 mL), washed with brine (2×10 mL), dried over Na$_2$SO$_4$, and concentrated in vacuo. The residue was purified by SiO$_2$ flash column chromatography using 20% EtOAc/hexanes as eluent to give methyl ester 17 (130 mg, 86%). TLC: 50% EtOAc/hexanes, R$_f$~0.41; $^1$H NMR (CDCl$_3$, 300 MHz) δ 5.95 (bs, 1H), 5.50-5.30 (m, 2H), 4.05 (d, 2H, J=5.2 Hz), 3.76 (s, 3H), 3.41 (t, 2H, J=6.7 Hz), 3.39 (t, 2H, J=7.3 Hz), 2.31 (q, 2H, J=6.7 Hz), 2.24 (t, 2H, J=7.3 Hz), 2.03 (apparent q, 2H, J=6.7 Hz), 1.70-1.50 (m, 4H), 1.40-1.22 (m, 18H), 0.87 (t, 3H, J=6.7 Hz); $^{13}$C NMR (CDCl$_3$, 75 MHz) δ 173.25, 170.44, 131.55, 125.44, 70.86, 70.30, 52.13, 40.98, 36.13, 31.73, 29.59, 29.41, 29.36, 29.28, 29.12, 28.97, 28.81, 27.82, 27.08, 26.02, 25.37, 22.51, 13.96.

Lithium hydroxide (1 mL of a 1 N aq. soln, 1 mmol) was added dropwise with stirring to a solution of methyl ester 14 (130 mg, 0.33 mmol) in THF (4 mL) and water (1 mL) at 0° C. After stirring overnight at room temperature, the reaction mixture was cooled to 0° C., acidified carefully with 1 M aq. oxalic acid to pH 5 and extracted with ethyl acetate (30 mL). The combined organic extracts were washed with water (2×15 mL), brine (2×15 mL), dried over Na$_2$SO$_4$, and concentrated under reduced pressure. The residue which was purified by column chromatography eluting in 30% EtOAc/hexanes to give 15 (120 mg, 95%). TLC: 50% ethyl acetate/hexanes, R$_f$~0.04; $^1$H NMR (CDCl$_3$, 300 MHz) δ 6.10 (bs, 1H), 5.50-5.29 (m, 2H), 4.07 (d, 2H, J=5.2 Hz), 3.45 (t, 2H, J=6.4 Hz), 3.42 (t, 2H, J=7.3 Hz), 2.33 (apparent q, 2H, J=7.3 Hz), 2.26 (t, 2H, J=7.3 Hz), 2.03 (apparent q, 2H, J=6.7 Hz). 1.70-1.52 (m, 4H), 1.40-1.22 (m, 18H), 0.88 (t, 2H, J=6.4 Hz).

Synthesis of Derivative 22 ((Z)-2,3,4,5,6-pentahydroxyhexyl 11-(nonyloxy) undec-8-enoate (TVR-II-007-20)).

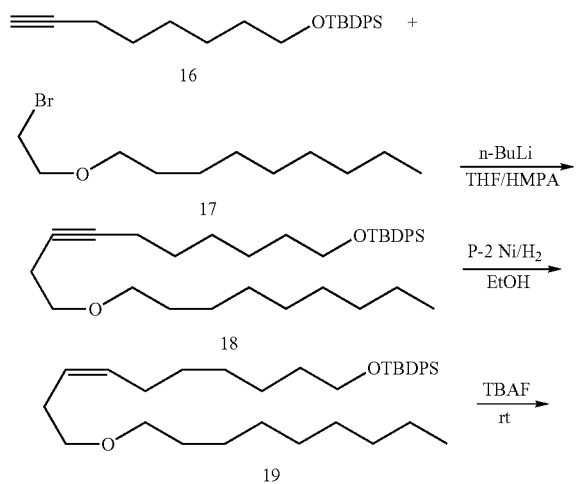

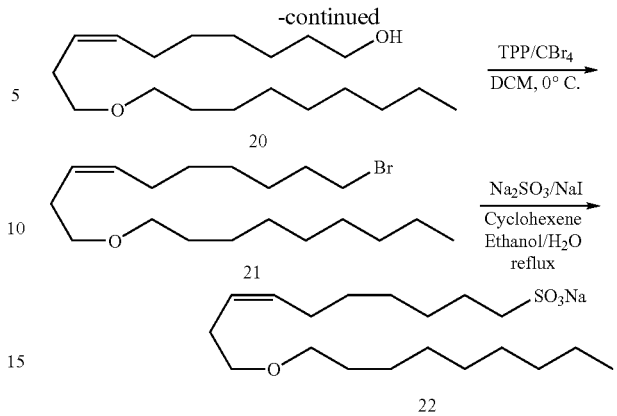

The synthesis of Derivative 22 ((Z)-2,3,4,5,6-pentahydroxyhexyl 11-(nonyloxy)undec-8-enoate (TVR-II-007-20)) is shown above. n-BuLi (1.5 mL of a 2.5 M hexane soln, 3.7 mmol) was added dropwise to a −78° C. solution of 16 (0.67 g, 1.85 mmol)(Daines et al., 1994, J. Med. Chem., 37:3327-36; Yu et al., 2003, Bioorg. Med. Chem. 11:2803-21) in dry THF/HMPA (4:1, 8 mL) under an argon atmosphere. After stirring at −78° C. for 30 minutes and at 0° C. for 1 hour, the reaction mixture was re-cooled to −78° C. and a solution of 17 (0.36 g, 1.43 mmol)(Falck et al., 2003, Bioorg. Med. Chem. Lett. 13:4011-14) in dry THF (4 mL) was added. The reaction mixture was warmed to room temperature over 3 hours, stirred at that temperature for another 12 hours, quenched with sat. aqueous NH$_4$Cl (5 mL), acidified to pH 4 with 1M oxalic acid, and extracted into EtOAc (2×30 mL). The combined organic extracts were washed with water (2×10 mL), brine (10 mL), dried over anhydrous Na$_2$SO$_4$, and concentrated in vacuo. The residue was purified by silica gel column chromatography to afford 18 (0.59 g, 74%). TLC: 10% EtOAc/hexanes, R$_f$~0.64; $^1$H NMR (CDCl$_3$, 400 MHz) δ 7.78-7.64 (m, 4H), 7.44-7.34 (m, 6H), 3.65 (t, 2H, J=6.4 Hz), 3.49 (t, 2H, J=7.0 Hz), 3.43 (t, 2H, J=6.7 Hz), 2.45-2.39 (m, 2H), 2.15-2.09 (m, 2H), 1.60-1.20 (m, 22H), 1.04 (s, 9H), 0.87 (t, 3H, J=6.7 Hz).

NaBH$_4$ (11 mg, 0.28 mmol) was added to a suspension of Ni(OAc)$_2$ (70 mg, 0.28 mmol) in absolute ethanol (1 mL) under a H$_2$ atmosphere. After 15 min, distilled ethylenediamine (34 μL, 0.56 mmol) was added, and after an additional 15 minutes, a solution of 18 (0.59 g, 1.12 mmol) in absolute ethanol (2 mL) was added. After 1 hour, the reaction was diluted with ether (5 mL), filtered through a small bed of silica gel, and the filtrate was concentrated under reduced pressure. The residue was purified by SiO$_2$ flash chromatography using 1% EtOAc/hexanes to furnish 19 (0.55 g, 93%). TLC: 5% EtOAc/hexanes, R$_f$~0.48; $^1$H NMR (CDCl$_3$, 400 MHz) δ 7.70-7.62 (m, 4H), 7.42-7.36 (m, 6H), 5.45-5.30 (m, 2H), 3.79 (t, 2H, J=7.1 Hz), 3.54-3.30 (m, 4H), 2.24-2.16 (m, 4H), 1.54-1.20 (m, 22H), 0.98 (s, 9H), 0.87 (t, 3H, J=7.0 Hz).

A solution of tetra-n-butylammonium fluoride (1.14 mL of a 1 M THF soln, 1.14 mmol) was added to a 0° C. solution of 19 (0.55 g, 1.03 mmol) in THF (10 mL) under an argon atmosphere. After stirring overnight, the reaction mixture was diluted with Et$_2$O (100 mL), washed with water (2×30 mL), brine (20 mL), dried over Na$_2$SO$_4$, and concentrated under reduced pressure. The residue was purified by SiO$_2$ flash chromatography eluting with 10% EtOAc/hexanes to furnish 20 (0.284 g, 92%). TLC: 30% EtOAc/hexanes, R$_f$~0.48; $^1$H NMR (CDCl$_3$, 300 MHz) δ 5.50-5.32 (m, 2H), 3.68-3.60

(apparent q, 2H, J=6.4 Hz), 3.41 (t, 2H, J=6.7 Hz), 3.40 (t, 2H, J=7.3 Hz), 2.32 (q, 2H, J=6.7, 7.0 Hz), 2.10-2.00 (apparent q, 2H, J=6.4 Hz), 1.62-1.50 (m, 2H), 1.42-1.22 (m, 20H), 0.87 (t, 3H, J=6.7 Hz).

Triphenylphosphine (0.38 g, 1.47 mmol) was added to a 0° C. solution of 20 (0.28 g, 1.05 mmol) in dry CH$_2$Cl$_2$ (5 mL) followed after 10 minutes by carbon tetrabromide (0.42 g, 1.26 mmol). The resulting yellow reaction mixture was stirred at 0° C. for 1 hour, then the solvent was concentrated under reduced pressure. The residue was purified by silica gel column chromatography eluting with 1% EtOAc/hexanes to afford 21 (0.30 g, 87%). TLC: 10% EtOAc/hexanes, R$_f$-0.71; $^1$H NMR (CDCl$_3$, 300 MHz) δ 5.51-5.33 (m, 2H), 3.44-3.37 (m, 6H), 2.32 (q, 2H, J=6.4 Hz), 2.05 (q, 2H, J=6.7 Hz), 1.85 (quintet, 2H, J=7.0 Hz), 1.63-1.51 (m, 2H), 1.49-1.22 (m, 18H), 0.88 (t, 3H, J=6.4 Hz).

Sodium sulphite (280 mg, 2.22 mmol), sodium iodide (80 mg, 0.55 mmol), and cyclohexene (33 µL, 0.55 mmol) were added sequentially to a solution of 21 (200 mg, 0.55 mmol) in ethanol/water (4:1, 5 mL). After stirring under reflux for 12 hours, undissolved sodium sulphite was removed by filtration, and the ethanol/water were evaporated in vacuo. The residue was purified by SiO$_2$ flash column chromatography with hexanes/EtOAc/MeOH (4:1:0.6) to give 22 (50 mg, 24%) plus about 30% impure material which could be recycled. TLC: EtOAc/hexanes/MeOH (2:1:0.6), R$_f$-0.51; $^1$H NMR (CD$_3$OD, 300 MHz) δ 5.55-5.32 (m, 2H), 3.45-3.37 (m, 4H), 2.82-2.74 (m, 2H), 2.34-2.18 (m, 2H), 2.10-1.94 (m, 2H), 1.84-1.71 (m, 2H), 1.60-1.48 (m, 2H), 1.45-1.25 (m, 18H), 0.89 (t, 3H, J=6.4 Hz).

Synthesis of Ether 29 Derivative ((Z)-14-(hexyloxy) tetradec-5-enoate (SB-II-148-33))

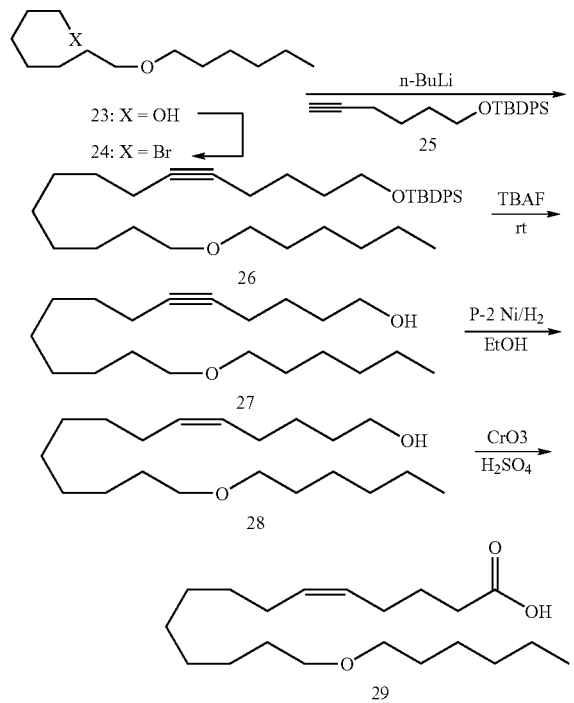

The synthesis of Ether 29 Derivative ((Z)-14-(hexyloxy) tetradec-5-enoate (SB-II-148-33)) is shown above. Triphenylphosphine (5.74 g, 21.91 mmol) was added to a 0° C. solution of 23 (3.60 g, 15.65 mmol)(Weissberg et al., 2001, J. Combinatorial Chem. 3:154-56) in dry CH$_2$Cl$_2$ (25 mL) followed after 10 minutes by carbon tetrabromide (6.74 g, 20.37 mmol). The resulting yellow reaction mixture was stirred at 0° C. for 1 hour, and then the solvent was concentrated under reduced pressure. The residue was purified by silica gel column chromatography eluting with 1% EtOAc/hexanes to afford 24 (4.1 g, 90%). TLC: 20% EtOAc/hexanes, R$_f$-0.61; $^1$H NMR (CDCl$_3$, 400 Mhz) δ 3.36-3.44 (m, 6H), 1.86 (q, 2H, J=6.7 Hz), 1.57 (quintet, 4H, J=6.7 Hz), 1.24-1.50 (m, 12H), 0.89 (t, 3H, J=7.1 Hz).

n-Butyl lithium (Aldrich, 2.5 M in hexanes, 3.30 mL, 8.22 mmol) was added dropwise to a -78° C. solution of 25 (2.76 g. 8.22 mmol)(Romeril et al., 2005, Tetrahedron 61:1127-40) in a mixture of dry THF/HMPA (4:1, 50 mL) under an argon atmosphere and stirred for 30 minutes at -78° C. and then at 0° C. for 2 hours. A -78° C. solution of bromide 24 (2 g, 6.84 mmol) in dry THF (10 mL) was cannulated into the above reaction mixture. After stirring at -78° C. for 1 hour, the mixture was gradually warmed to room temperature and stirred overnight. The reaction mixture was re-cooled to 0° C. and quenched with saturated aq. ammonium chloride solution. The aqueous layer was acidified to pH 4 with oxalic acid solution (1M) and extracted with ether (3×100 mL). The combined ethereal extracts were washed with water (3×50 mL), brine (2×50 mL), dried over Na$_2$SO$_4$, and concentrated under reduced pressure. The residue was purified by SiO$_2$ flash chromatography with 5% EtOAc/hexanes to furnish silyl ether 26 (2.20 g, 62%). TLC: 10% ethyl acetate/hexanes, R$_f$-0.62; $^1$H NMR (CDCl$_3$, 400 MHz) δ 7.71-7.64 (m, 4H), 7.46-7.35 (m, 6H), 3.68 (t, 2H, J=6.2 Hz), 3.39 (t, 4H, J=7.0 Hz), 2.20-2.11 (m, 4H), 1.72-1.20 (m, 24H), 1.06 (s, 9H), 0.89 (t, 3H, J=7.0 Hz).

A solution of tetra-n-butylammonium fluoride (8.20 mL of a 1 M TLF soln, 8.20 mmol) was added to a 0° C. solution of 26 (2.20 g, 4.02 mmol) in THF (30 mL) under an argon atmosphere. After stirring for 5 hours, the reaction mixture was diluted with Et$_2$O (150 mL), washed with water (2×60 mL), brine (60 mL), dried over Na$_2$SO$_4$, and concentrated under reduced pressure. The residue was purified by SiO$_2$ flash chromatography eluting with 10% ethyl acetate/hexanes to furnish alcohol 27 (1.04 g, 83%). TLC, 30% EtOAc/hexanes, R$_f$-0.48; $^1$H NMR (CDCl$_3$, 400 MHz) δ 3.67 (apparent q, 2H, J=6.4 Hz), 3.40 (t, 4H, J=6.7 Hz), 2.24-2.10 (m, 4H), 1.72-1.24 (m, 24H), 0.89 (t, 3H, J=7.0 Hz).

NaBH$_4$ (16 mg, 0.48 mmol) was added to a suspension of Ni(OAc)$_2$ (116 mg, 0.48 mmol) in absolute ethanol (10 mL) under a H$_2$ atmosphere. After 15 minutes, distilled ethylenediamine (60 µL, 0.96 mmol) was added, and after an additional 15 minutes, a solution of 27 (1.00 g, 3.22 mmol) in absolute ethanol (10 mL) was added. After 1 hour, the reaction was diluted with ether (25 mL), filtered through a small bed of silica gel, and the filtrate was concentrated under reduced pressure. The residue was purified by SiO$_2$ flash chromatography using 20% EtOAc/hexanes to furnish 28 (0.91 g, 92%). TLC: 30% EtOAc/hexanes, R$_f$-0.35; $^1$H NMR (CDCl$_3$, 400 MHz) δ 5.43-5.31 (m, 2H), 3.65 (apparent q, 2H, J=6.4 Hz), 3.40 (t, 4H, J=6.7 Hz), 2.10-1.98 (m, 4H), 1.62-1.52 (m, 6H), 1.48-1.22 (m, 18H), 0.89 (t, 3H, J=6.7 Hz); $^{13}$C NMR (CDCl$_3$, 75 MHz) δ 130.49, 129.52, 71.15, 71.12, 62.95, 32.54, 31.89, 29.92, 29.88, 29.84, 29.70, 29.62, 29.37, 27.36, 27.09, 26.34, 26.04, 26.03, 22.80, 14.22.

A solution of alcohol 28 (0.91 g, 2.91 mmol) in acetone (30 mL) was added dropwise over 1 hour to a -30° C. solution of Jones reagent in acetone (0.12 M, 11 mL, 14.58 mmol). After another 1 hour at the same temperature, the reaction mixture was warmed to 0° C. After 3 hours, the reaction mixture was quenched by the addition of excess iso-propanol and the green inorganic solids were removed by filtration. The filtrate cake was washed with acetone. The combined filtrate and acetone washes were concentrated in vacuo. The residue was dissolved in EtOAc (60 mL), washed with water (2×30 mL), brine (30 mL), dried over $Na_2SO_4$, and concentrated under reduced pressure. The residue was purified by $SiO_2$ flash chromatography eluting with 20% EtOAc/hexanes to furnish compound 29 (0.87 g, 74%). TLC: 30% EtOAc/hexane $R_f$-0.32.; $^1$H NMR ($CDCl_3$, 400 MHz) δ 5.29-5.48 (m, 2H), 3.42 (t, 4H, J=6.7 Hz), 2.36 (t, 2H, J=7.3 Hz ), 2.11 (q, 2H, J=7.0 Hz ), 2.01 (q, 2H, J=7.1 Hz), 1.70 (q, 2H, J=7.3 Hz ), 1.57 (q, 2H, J=7.3 Hz), 1.25-1.38 (m, 18H), 0.89 (t, 3H, J=7.1 Hz).

Example 2

Effect of Epoxide Metabolite Derivatives on Angiotensin II Infused Hypertension Male Sprague-Dawley rats (Charles River Laboratories, Wilmington, Mass., USA) were housed separately in cages and maintained under temperature- and light-controlled conditions. Throughout the experiments, animals had free access to standard rat chow. Surgical procedures were performed on pentobarbital (40 mg/kg body weight, i.p.) anaesthetized animals using sterile procedures. Rats weighing 180-200 g were divided into two experimental groups: one group received sham surgery, and a second group was subjected to angiotensin II infusion. Angiotensin II was infused at a continuous rate via an osmotic minipump (60 ng/min; model 2002, ALZA Corp. Palo Alto, Calif., USA) implanted subcutaneously at the dorsum of the neck. Systolic blood pressure was measured in conscious rats by tail-cuff plethysmography to monitor the progression of hypertension.

Experiments were performed using the in vitro perfused juxtamedullary nephron technique on rats 12-14 days after surgical manipulations. Animals were anaesthetized with sodium pentobarbital; the right carotid artery was cannulated; and a midline abdominal incision was made. The right renal artery was cannulated via the superior mesenteric artery, and perfusion of the kidney was immediately initiated. The kidney was perfused with a Tyrode solution containing 6% albumin and a mixture of 1-amino acids. Blood was collected through the carotid artery cannula into a heparinized saline syringe (2000 U). Erythrocytes were separated from plasma and leukocytes by centrifugation, as previously described (Imig and Deichmann, 1997, Renal Physiol. 273:F274-282). The supernatant was removed and washed twice with 0.9% NaCl containing 0.2% dextrose (pH 7.0). The red blood cells were added to a Tyrode solution containing 6% albumin to attain a haematocrit of 20%. The solution was filtered and stirred continuously in a closed reservoir that was pressurized by a 95% O2 to 5% CO2 tank. After collection of the blood, the kidney was removed from the rat and maintained in an organ chamber at room temperature throughout the isolation and dissection procedure. The juxtamedullary vasculature was isolated as previously described (Imig and Deichmann, 1997). Upon completion of the microdissection procedures, the Tyrode solution was replaced by the blood solution, and renal artery perfusion pressure measured at the tip of the cannula was set to 100 mmHg. The organ chamber and bathing solution were warmed to 37° C., and the tissue surface was continuously superfused with a Tyrode solution containing 1% albumin.

Afferent arteriolar diameters were measured via video microscopy techniques. The isolated kidney was trans-illuminated on the fixed stage of a microscope equipped with a 75-W xenon lamp and a 40×water immersion objective. Images of the blood vessel under study were captured by a Newvicon camera, passed through a time-date generator and image enhancing system, displayed on a monitor, and videotaped for later analysis. Vessel diameter was measured using a digital image-shearing monitor that was calibrated by a stage micrometer and measurements were reproducible within 0.5 μm.

After an equilibration period, the proximal portion of two to six afferent arterioles were chosen for study of each compound's effect. Measurements of afferent arteriolar diameter were made for a 5 minute period at a site at least 50 μm from any branch point. The control vascular diameter at a renal perfusion pressure of 100 mmHg over a 5 minute period was determined. Norepinephrine (0.5 μmol/l, Sanofi/Winthrop Pharmaceuticals, San Diego, Calif., USA) was added to the perfusate to elevate basal tone. Following norepinephrine treatment, the afferent arteriole response to superfusion of the epoxide metabolite compounds was determined at varying concentrations. The superfusate was returned to the control solution for 10 minutes, and vessel diameter was allowed to recover. Renal perfusion pressure was then increased to 150 mmHg, and the response to superfusion of the epoxide metabolite compounds was determined again. Steady-state diameter was attained by the end of 2 minutes, and the average diameter at 3-5 minutes for each of the epoxide metabolite derivative compounds was utilized for statistical analysis. Each of the tested epoxide metabolite derivative compounds increased the dilation of the afferent arterioles at a rate similar to or greater than the control epoxide metabolite (FIGS. 1A-1H). The epoxide metabolite derivative compounds were synthesized as described above.

Alternative method for measurement of effect: Control afferent arteriolar diameter measurements are made at a renal perfusion pressure of 100 mmHg as described above. Angiotensin II (0.1-10 nmol/l) is subsequently delivered by superfusion for 3 minutes, and a cumulative concentration curve is obtained. The vessel is allowed to recover, and the response to angiotensin II is determined at a renal perfusion pressure of 150 mmHg. Next, renal perfusion pressure is lowered to 100 mmHg and the epoxide metabolite derivative test compound (100 nmol/l) is delivered by superfusion. Based on measured tissue and urine EET levels, as well as biological activity, it is determined whether 100 nmol/l of the test compound is within the physiological range. The afferent arteriolar response to angiotensin II is re-assessed at the two renal perfusion pressures in the continued presence of the test compound. Steady-state diameter is attained by the end of 2 minutes, and the average diameter at 3 minutes for each angiotensin II concentration is utilized for statistical analysis.

Example 3

Effect of Epoxide Metabolite Derivatives on Spontaneously Hypertensive Rat

As the 11-nonyloxy-undec-8(Z)-enoic acid derivatives lowered blood pressure in angiontensin hypertension, additional experiments were performed to determine if one of the derivatives could lower blood pressure in another hypertension model system. Male spontaneously hypertensive rats (SHRs) were maintained on a 12-hour light-dark cycle and allowed access to food and water ad libitum. These studies complied with the protocols for animal use outlined by the American Physiological Society and were approved by the institutional animal care and use committee.

Rats from 6 to 12 weeks of age were treated with 11-nonyloxy-undec-8(Z)-enoic acid derivative (TVR-I-276-21)( 2 mg/d i.p.) or vehicle for 8 days. Blood pressure was measured at Day 0, Day 4, and Day 8. Blood pressure significantly increased from control levels in the SHRs that were administered vehicle. In contrast, the blood pressure of the SHRs that were treated with TVR-I-276-21 (2 mg/d i.p.) did not increase to the same extent as those that received the vehicle treatment. These data provide further evidence that 11-nonyloxy-undec-8(Z)-enoic acid derivatives can lower blood pressure in art-accepted animal model systems for hypertension.

Example 4

Synthesis of Amino Acid Derivatives 32 and 34

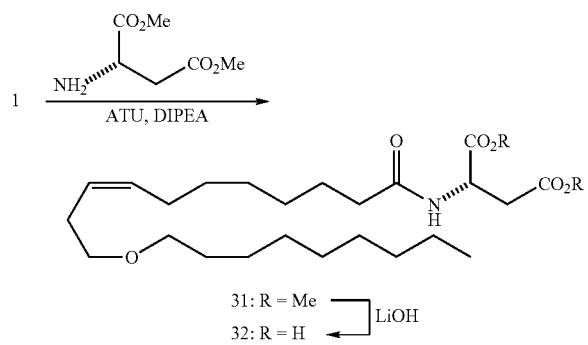

The synthesis of Derivative 32 ((Z)-2-(11-(nonyloxy)undec-8-enamido) succinic acid (SA-III-161-32)) is shown above. According to the procedure described for preparation of 14, O-(7-azabenzotriazol-1-yl)-N,N,N',N'-tetramethyluronium hexafluorophosphate (204 mg, 0.53 mmol), acid 1 (155 mg, 0.47 mmol), L-Aspartic acid methyl ester (106 mg, 0.53 mmol) and N,N-diisopropylethylamine (200 µL, 1.53 mmol) in dry DMF (6 mL) were used to prepare 31 (0.19 g, 82%). TLC: 50% EtOAc/hexanes, $R_f$~0.45; $^1$H NMR (CDCl$_3$, 300 MHz) δ 6.46 (d, 1H, J=8.1 Hz), 5.45-5.31 (m, 2H), 4.87-4.81 (m, 1H), 3.73 (s, 3H), 3.66 (s, 3H), 3.40-3.34 (m, 4H), 3.03 (dd, 1H, J=17, 4.2 Hz), 2.82 (dd, 1H, J=17.1, 4.2 Hz), 2.32-2.25 (m, 2H) 2.19 (t, 2H, J=7.2 Hz), 2.06-1.97 (m, 2H), 1.62-1.48 (m, 4H), 1.35-1.19 (m, 18H), 0.84 (t, 3H, J=6.3 Hz).

1N Lithium hydroxide solution (2.5 mL, 2.5 mmol) was added dropwise while stirring to a solution of methyl ester 31 (210 mg, 0.41 mmol) in THF (4 mL) and water (1 mL) as described for compound 15 to give 32 (174 mg, 88%). TLC: neat ethyl acetate, $R_f$~0.15; $^1$H NMR (CDCl$_3$, 300 MHz) δ 6.88 (d, 1H, J=7.5 Hz), 5.46-5.24 (m, 2H), 4.90-4.84 (m, 1H), 4.12 (q, 2H, J=6.9 Hz), 3.47-3.41 (m, 4H), 3.03 (dd, 1H, J=17, 4.2 Hz), 2.82 (dd, 1H, J=17.1, 4.2 Hz), 2.36-2.23 (m, 4H), 2.08-1.99 (m, 6H), 1.61-1.53 (m, 4H), 1.39-1.20 (m, 20H), 0.86 (t, 3H, J=6.6 Hz).

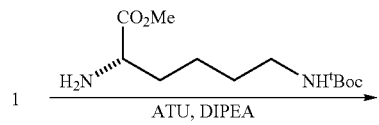

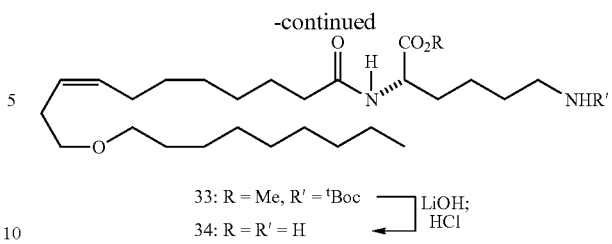

The synthesis of Derivative 34 ((Z)-6-amino-2-(11-(nonyloxy)undec-8-enamido)hexanoic acid (SA-III-172-26)) is shown above. According to the procedure described for preparation of 14, O-(7-azabenzotriazol-1-yl)-N,N,N',N'-tetramethyluronium hexafluorophosphate (224 mg, 0.58 mmol), acid 1 (170 mg, 0.52 mmol), ε-$^t$Boc protected lysine methyl ester (153 mg, 0.58 mmol) and diisopropylethylamine (200 µL, 1.53 mmol) in dry DMF (6 mL) were used to prepare 33 (0.20 g, 68%). TLC: 80% EtOAc/hexanes, $R_f$~0.75; $^1$H NMR (CDCl$_3$, 300 MHz) δ 6.07 (d, 1H, J=6.9 Hz), 5.44-5.32 (m, 2H), 4.62-4.54 (m, 2H), 3.72 (s, 3H), 3.45-3.34 (m, 4H), 3.12-3.04 (m, 2H), 2.30 (q, 2H, J=6.9 Hz), 2.20 (t, 2H, J=7.8 Hz), 2.04-2.00 (m, 2H), 1.64-1.42 (m, 17H), 1.35-1.24 (m, 20H), 0.85 (t, 3H, J=6.6 Hz).

1N Lithium hydroxide solution (2.0 mL, 2.0 mmol) was added dropwise while stirring to a solution of methyl ester 33 (200 mg, 0.35 mmol) in THF (4 mL) and water (1 mL) as described for compound 15 to give as residue which was subjected to $^t$Boc-deprotection in THF:H$_2$O (1:1, 5 mL) saturated with HCl gas. The solvent was evaporated and dried in high vacuum for 2h to give 34 as the hydrochloride salt (35 mg, 20%). $^1$H NMR (CD$_3$OD, 300 MHz) δ 5.48-5.30 (m, 2H), 4.42-4.34 (m, 1H), 3.46-3.38 (m, 4H), 3.12-2.95 (m, 2H), 2.34-2.20 (m, 4H), 2.08-1.24 (m, 28H), 0.88 (t, 3H, J=6.6 Hz).

Example 5

Effect of Derivatives 32 and 34 on Spontaneously Hypertensive Rats

The blood pressure lowering effects of these analogs were analyzed in an established model of hepertension, the spontaneously hypertensive rats (SHR) using telemetry. As discussed above, 11,12-ether EET-8-ZE failed to lower blood pressure in SHR; however, esterification of the carboxylic group of 11,12-ether EET-8-ZE prevented blood pressure increase in SHR when injected at 2 mg/day for 12 days (MAO Δ change at day 8 of injection was −0.3±2 for treated and 12±1 mmHg for control SHR). As discussed in the previous example, additional derivatives with improved solubility and resistance to auto-oxidation and metabolism by sEH were designed using the pharmacophoric moiety of EET.

Figure 3A:
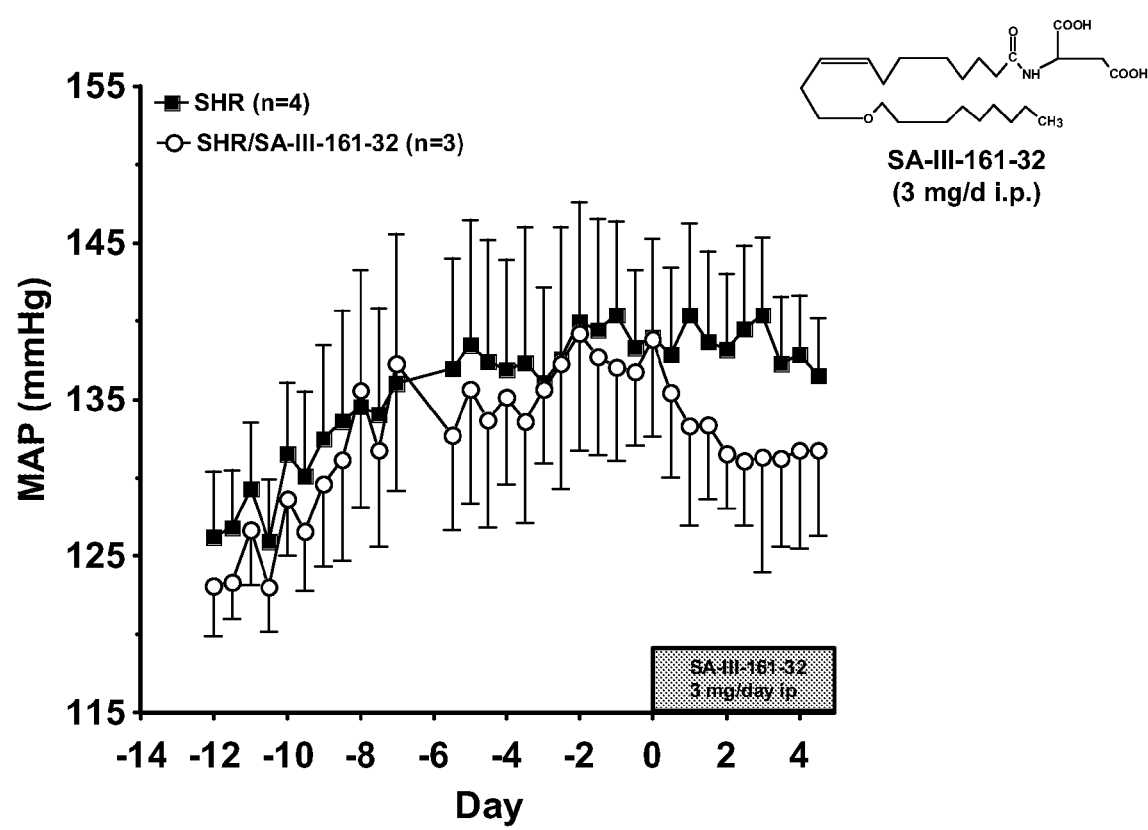
FIG. 3 shows the effect of the amide derivatives SA-III-161-32 and SA-III-172-26 on the mean arteriole pressure in spontaneously hypertensive rats (SHRs) as compared to the effect of vehicle alone. The chemical structure of the compound tested is shown above the graph. The effect of the compound is shown in the graph, and is represented as the mean arteriole pressure (mmHg). Panel A shows the results for SA-III-161-32, and Panel B shows the results for SA-III-172-26.
Figure 3B:
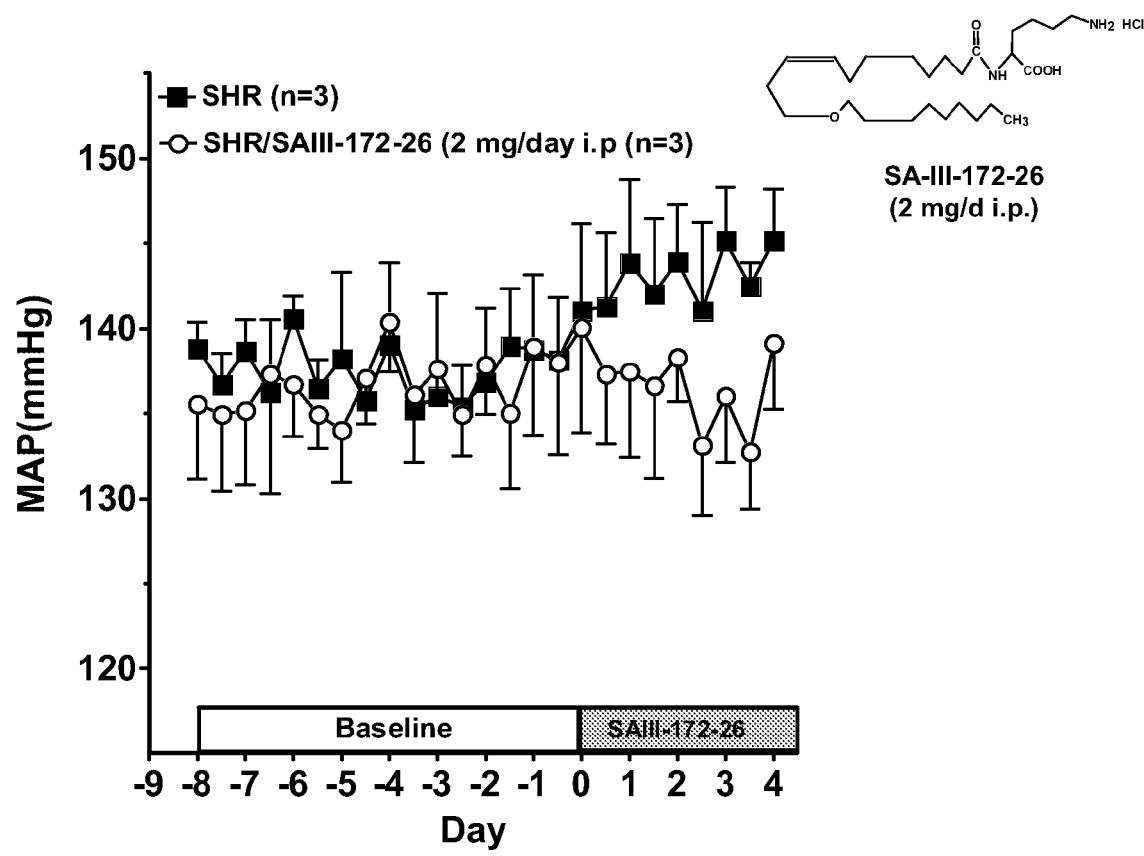

Amidation of the carboxylic group with aspartic acid produced another EET analog 32 (SA-III-161-32). This analog demonstrated a blood pressure lowering effect when injected at 3 mg/day in SHR for 5 days (MAP Δ change at day 2 of injection was −8±1.3 for treated and 1±1.3 mmHg in control SHR) (FIG. 3A). Amidation of the carboxylic group with lysine amino acid produced another EET analog 34 (SA-III-172-26). This analog exhibited a minimal blood pressure lowering effect when injected at 2 mg/day (FIG. 3B). These data suggest that amidation of the carboxylic group of 11,12-ether EET-8-ZE produced EET analogs capable of lowering blood pressure in SHR and provide further evidence to support the use of EET analogs in treatment of cardiovascular diseases.

We claim:

1. An 11,12-ether epoxyeicosatrienoic acid (EET) derivative compound, wherein the compound has the structural formula:

(I)

(II)

m = 0-3 or a pharmaceutically acceptable salt thereof, wherein
n is 1 to 4; m is 0 to 3;
$R_1$ is selected from the group consisting of a linear or branched alkyl and cycloalkyl, each having up to 10 carbon atoms;
$R_2$, in each occurrence, is selected from the group consisting of linear or branched alkyl, cycloalkyl, alkyloxy, alkylthio, alkylamino, alkenyl, alkoxycarbonyl, carboxyalkylamide, thiazolidinyl-2,4-dione, or heterocyclyl, each optionally substituted with one or more halogen, OH, $CO_2H$, $NH_2$, alkoxy, alkylamine, $NO_2$, $SO_3$alkyl, alkylthio, alkylsulfinyl, or alkylsulfonyl, and each having up to 12 carbon atoms; and
$R_3$ is a $C_{6-9}$ epoxide;
wherein the compound reduces blood pressure or hypertension caused by angiotensin II.

2. The compound of claim 1, wherein $R_2$ is selected from the group consisting of:

3. The compound of claim 2, wherein the compound is selected from the group consisting of:
(Z)-6-amino-2-(11-(nonyloxy)undec-8-enamido)hexanoic acid and
(Z)-2-(11-(nonyloxy)undec-8-enamido)succinic acid.

4. The compound of claim 3, wherein the compound is
(Z)-6-amino-2-(11-(nonyloxy)undec-8-enamido)hexanoic acid.

5. The compound of claim 3, wherein the compound is
(Z)-2-(11-(nonyloxy)undec-8-enamido)succinic acid.

6. A pharmaceutical composition comprising a therapeutically effective amount of a compound according to claim 1.

7. The pharmaceutical composition of claim 6, wherein the compound is selected from the group consisting of:
(Z)-6-amino-2-(11-(nonyloxy)undec-8-enamido)hexanoic acid and
(Z)-2-(11-(nonyloxy)undec-8-enamido)succinic acid.

8. The pharmaceutical composition of claim 7, wherein the compound is
(Z)-6-amino-2-(11-(nonyloxy)undec-8-enamido)hexanoic acid.

9. The pharmaceutical composition of claim 7, wherein the compound is
(Z)-2-(11-(nonyloxy)undec-8-enamido)succinic acid.

10. A method of treating a renal or cardiovascular disease caused by angiotensin II, said method comprising administering to a patient in need thereof a therapeutically effective amount of the compound of claim 1.

11. The method of claim 10, wherein the compound is selected from the group consisting of:
(Z)-6-amino-2-(11-(nonyloxy)undec-8-enamido)hexanoic acid and
(Z)-2-(11-(nonyloxy)undec-8-enamido)succinic acid.

12. The method of claim 11, wherein the compound is
(Z)6-amino-2-(11(nonyloxy)undec-8-enamido)hexanoic acid.

13. The method of claim 11, wherein the compound is
(Z)-2-(11-(nonyloxy)undec-8-enamido)succinic acid.

14. The method of claim 10, wherein the renal or cardiovascular disease involves endothelial dysfunction.

15. The method of claim 10, wherein the renal or cardiovascular disease is chosen from type 1 and type 2 diabetes, hepatorenal syndrome, metabolic syndrome, insulin resistance syndrome, glomerulonephritis, hypertension, congestive heart failure, heart attack, hypertensive heart disease, atherosclerosis, coronary artery disease, angina, ischemia, ischemic stroke, Raynaud's disease, and renal disease.

* * * * *

UNITED STATES PATENT AND TRADEMARK OFFICE
CERTIFICATE OF CORRECTION

PATENT NO. : 7,732,470 B2  Page 1 of 1
APPLICATION NO. : 12/040502
DATED : June 8, 2010
INVENTOR(S) : John D. Imig and John R. Falck It is certified that error appears in the above-identified patent and that said Letters Patent is hereby corrected as shown below:

At column 30, line 38, after comprising, delete "admin" and insert --admin- --.

Signed and Sealed this

Twenty-seventh Day of July, 2010

David J. Kappos
*Director of the United States Patent and Trademark Office*